(12) United States Patent  
Hoell, Jr. et al.

(10) Patent No.: US 9,707,003 B2
(45) Date of Patent: Jul. 18, 2017

(54) ARTICULATING SURGICAL INSTRUMENT

(75) Inventors: Joseph A. Hoell, Jr., Dunbarton, NH (US); David Carpenter, Jaffrey, NH (US)

(73) Assignee: Covidien LP, Mansfield, MA (US)

( * ) Notice: Subject to any disclaimer, the term of this patent is extended or adjusted under 35 U.S.C. 154(b) by 2134 days.

(21) Appl. No.: 12/189,954

(22) Filed: Aug. 12, 2008

(65) Prior Publication Data

US 2009/0088792 A1    Apr. 2, 2009

Related U.S. Application Data

(60) Provisional application No. 60/976,882, filed on Oct. 2, 2007.

(51) Int. Cl.
*A61B 17/29* (2006.01)
*A61B 17/00* (2006.01)

(52) U.S. Cl.
CPC ........ *A61B 17/29* (2013.01); *A61B 2017/003* (2013.01); *A61B 2017/00367* (2013.01); *A61B 2017/2902* (2013.01); *A61B 2017/292* (2013.01); *A61B 2017/2919* (2013.01); *A61B 2017/2925* (2013.01); *A61B 2017/2927* (2013.01); *A61B 2017/2929* (2013.01)

(58) Field of Classification Search
None
See application file for complete search history.

(56) References Cited

U.S. PATENT DOCUMENTS

| 4,203,430 A | 5/1980 | Takahashi |
| 4,207,873 A | 6/1980 | Kruy |
| 4,363,384 A * | 12/1982 | Richardson et al. ........ 188/72.7 |
| 4,374,525 A | 2/1983 | Baba |
| 4,483,326 A | 11/1984 | Yamaka et al. |
| 4,534,339 A | 8/1985 | Collins et al. |
| 4,610,383 A | 9/1986 | Rothfuss et al. |
| 4,872,456 A | 10/1989 | Hasson |
| 5,201,743 A | 4/1993 | Haber et al. |
| 5,209,747 A | 5/1993 | Knoepfler |
| 5,275,614 A | 1/1994 | Haber et al. |
| 5,282,806 A | 2/1994 | Haber et al. |
| 5,312,023 A | 5/1994 | Green et al. |
| 5,352,237 A | 10/1994 | Rodak et al. |
| 5,381,943 A | 1/1995 | Allen et al. |
| 5,395,327 A | 3/1995 | Lundquist et al. |

(Continued)

FOREIGN PATENT DOCUMENTS

| DE | 100 34 105 | 4/2002 |
| EP | 2027820 | 2/2009 |
| WO | WO2004/098701 | 11/2004 |

OTHER PUBLICATIONS

European Search Report for EP 08253193.0-2310 date of completion is Jun. 22, 2009 (3 pages).

*Primary Examiner* — Adam C Milligan

(57) ABSTRACT

A surgical instrument is provided having articulating, distal end rotation and tip rotational functions. The articulating function includes a wheel rotatable relative to a handle of the surgical instrument and operable to move an articulating section of the surgical instrument from a neutral or straight position to an articulated or bent position. The wheel incorporates a groove in the form of an Archimedes spiral to drive the articulating section between the neutral and bent positions.

16 Claims, 20 Drawing Sheets

(56) References Cited

U.S. PATENT DOCUMENTS

| | | |
|---|---|---|
| 5,403,342 A | 4/1995 | Tovey et al. |
| 5,454,827 A | 10/1995 | Aust et al. |
| 5,514,157 A | 5/1996 | Nicholas et al. |
| 5,549,637 A | 8/1996 | Crainich |
| 5,562,702 A | 10/1996 | Huitema et al. |
| 5,564,615 A | 10/1996 | Bishop et al. |
| 5,577,654 A | 11/1996 | Bishop |
| 5,588,581 A | 12/1996 | Conlon et al. |
| 5,601,224 A | 2/1997 | Bishop et al. |
| 5,626,553 A | 5/1997 | Frassica et al. |
| 5,626,587 A | 5/1997 | Bishop et al. |
| 5,634,584 A | 6/1997 | Okorocha et al. |
| 5,662,662 A | 9/1997 | Bishop et al. |
| 5,667,476 A | 9/1997 | Frassica et al. |
| 5,673,840 A | 10/1997 | Schulze et al. |
| 5,700,275 A | 12/1997 | Bell et al. |
| 5,704,534 A | 1/1998 | Huitema et al. |
| 5,766,196 A | 6/1998 | Griffiths |
| 5,860,995 A | 1/1999 | Berkelaar |
| 5,904,667 A | 5/1999 | Falwell |
| 5,921,956 A | 7/1999 | Grinberg et al. |
| 6,033,378 A | 3/2000 | Lundquist et al. |
| 6,063,098 A | 5/2000 | Houser et al. |
| 6,132,441 A | 10/2000 | Grace |
| 6,139,563 A | 10/2000 | Cosgrove, III et al. |
| 6,279,639 B1 * | 8/2001 | Schlecht et al. ............. 160/23.1 |
| 6,364,846 B1 | 4/2002 | Nakamura |
| 6,702,737 B2 | 3/2004 | Hino et al. |
| 6,858,005 B2 | 2/2005 | Ohline et al. |
| 6,991,627 B2 | 1/2006 | Madhani et al. |
| 7,111,769 B2 | 9/2006 | Wales et al. |
| 7,144,401 B2 | 12/2006 | Yamamoto et al. |
| 7,223,276 B2 | 5/2007 | List et al. |
| 7,543,731 B2 | 6/2009 | Green et al. |
| 2007/0152014 A1 | 7/2007 | Gillum et al. |
| 2007/0162072 A1 | 7/2007 | Nicholas et al. |

* cited by examiner

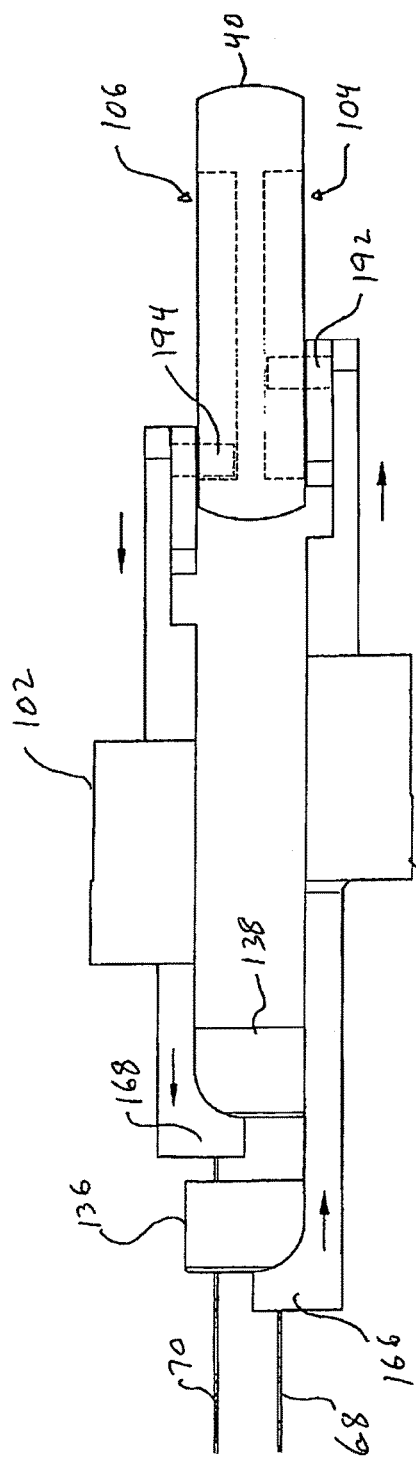
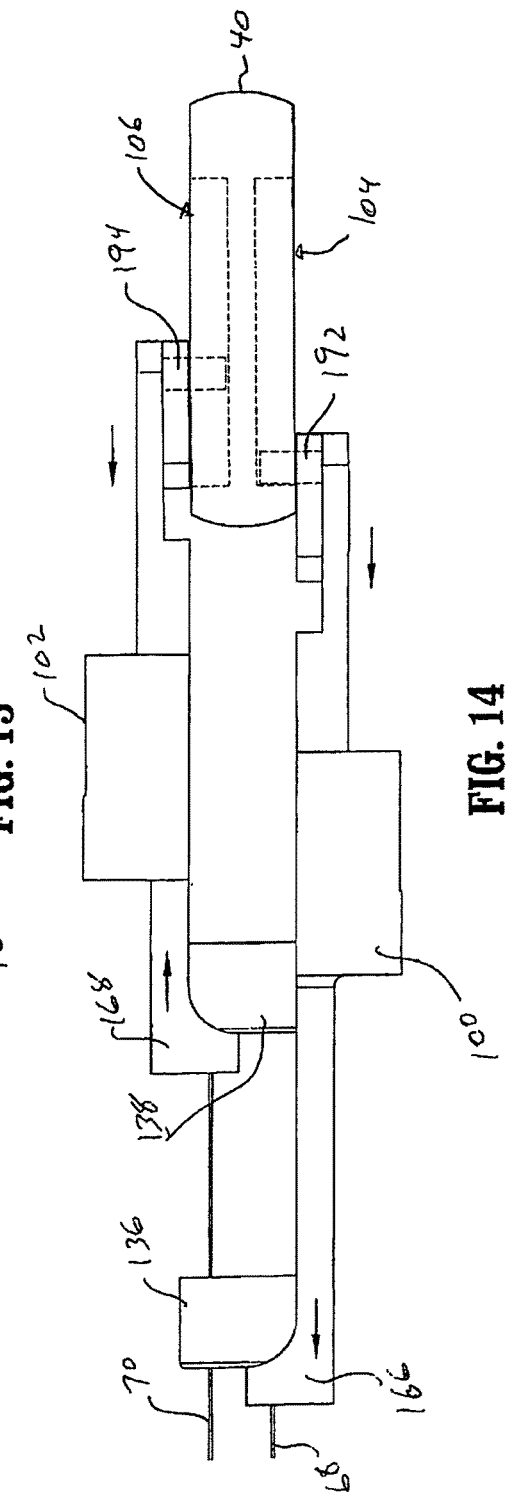

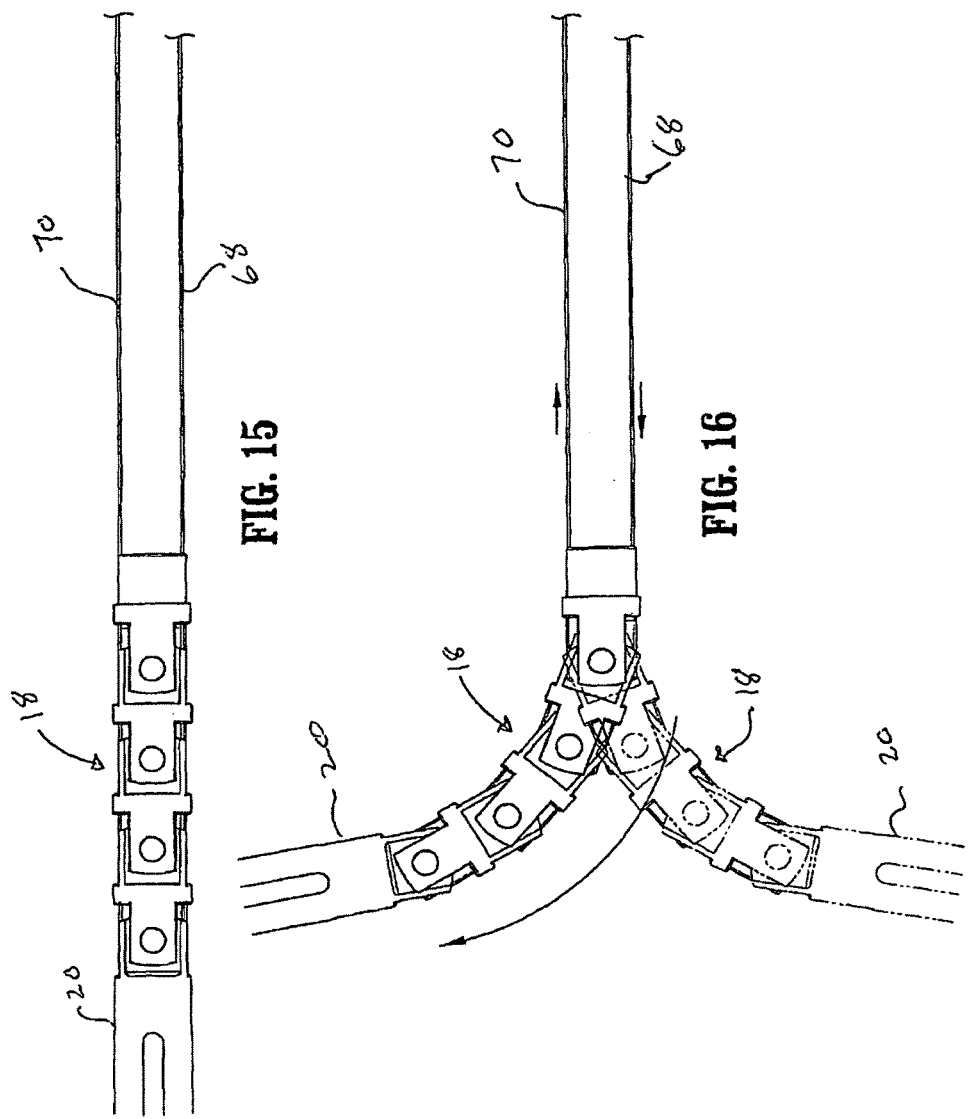

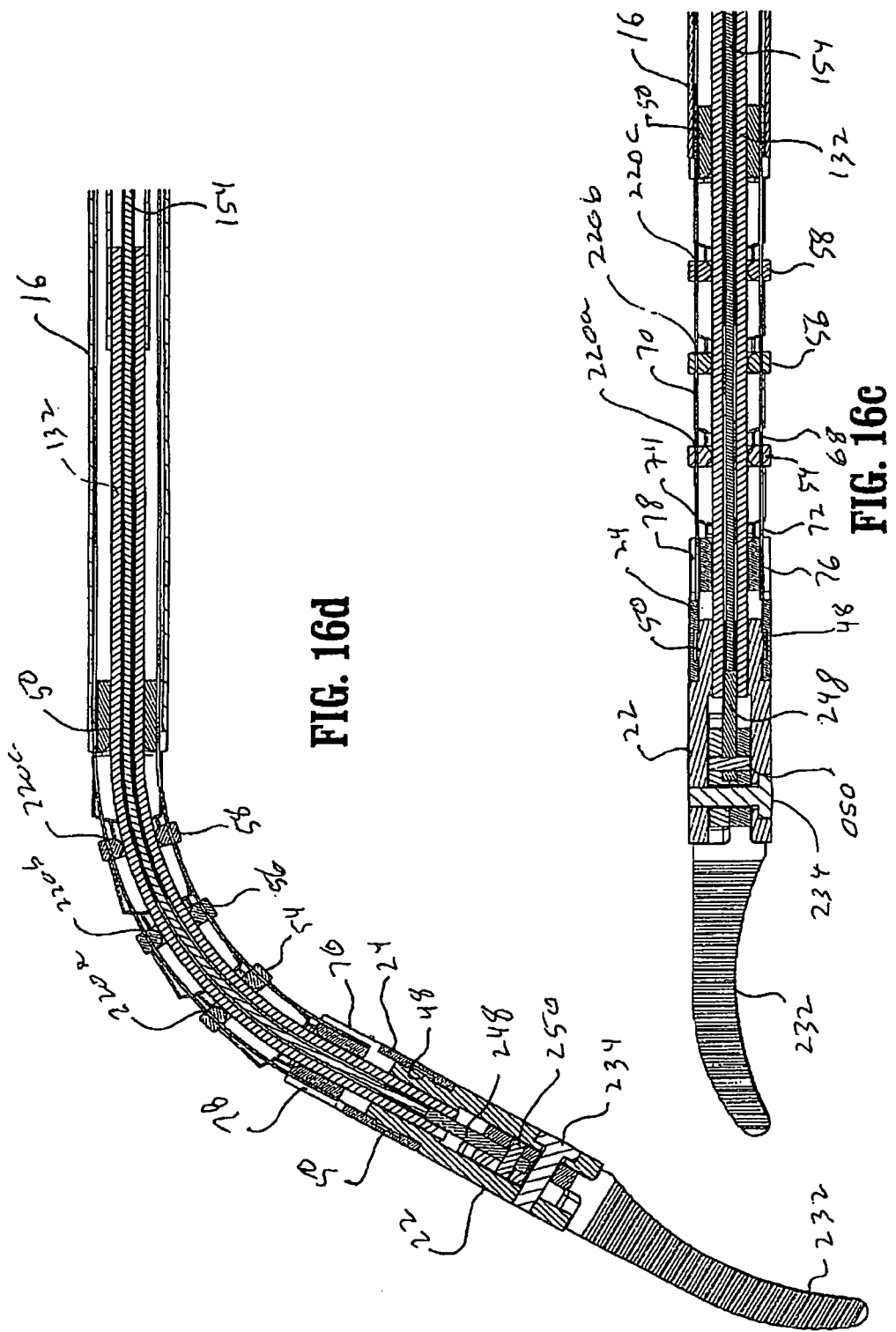

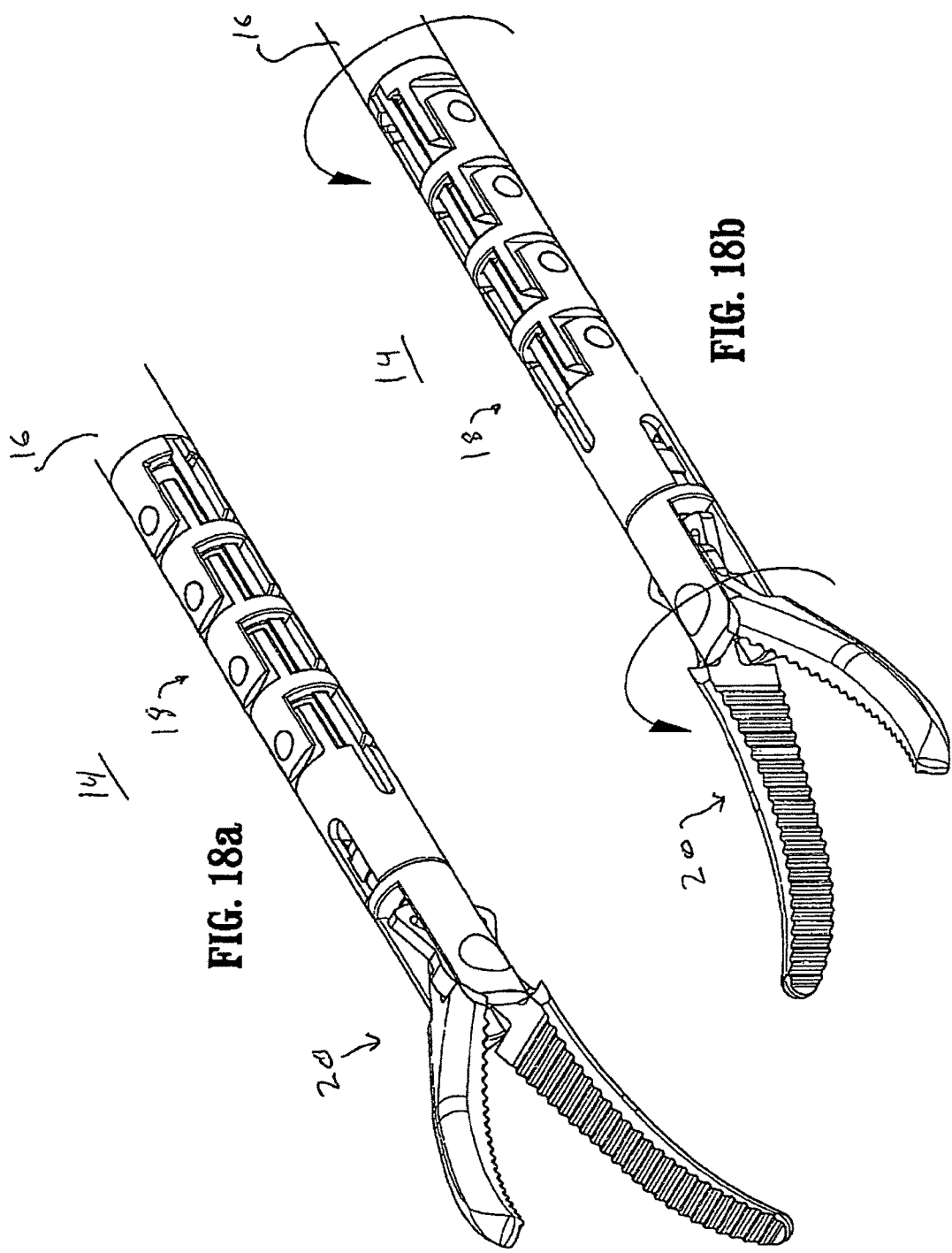

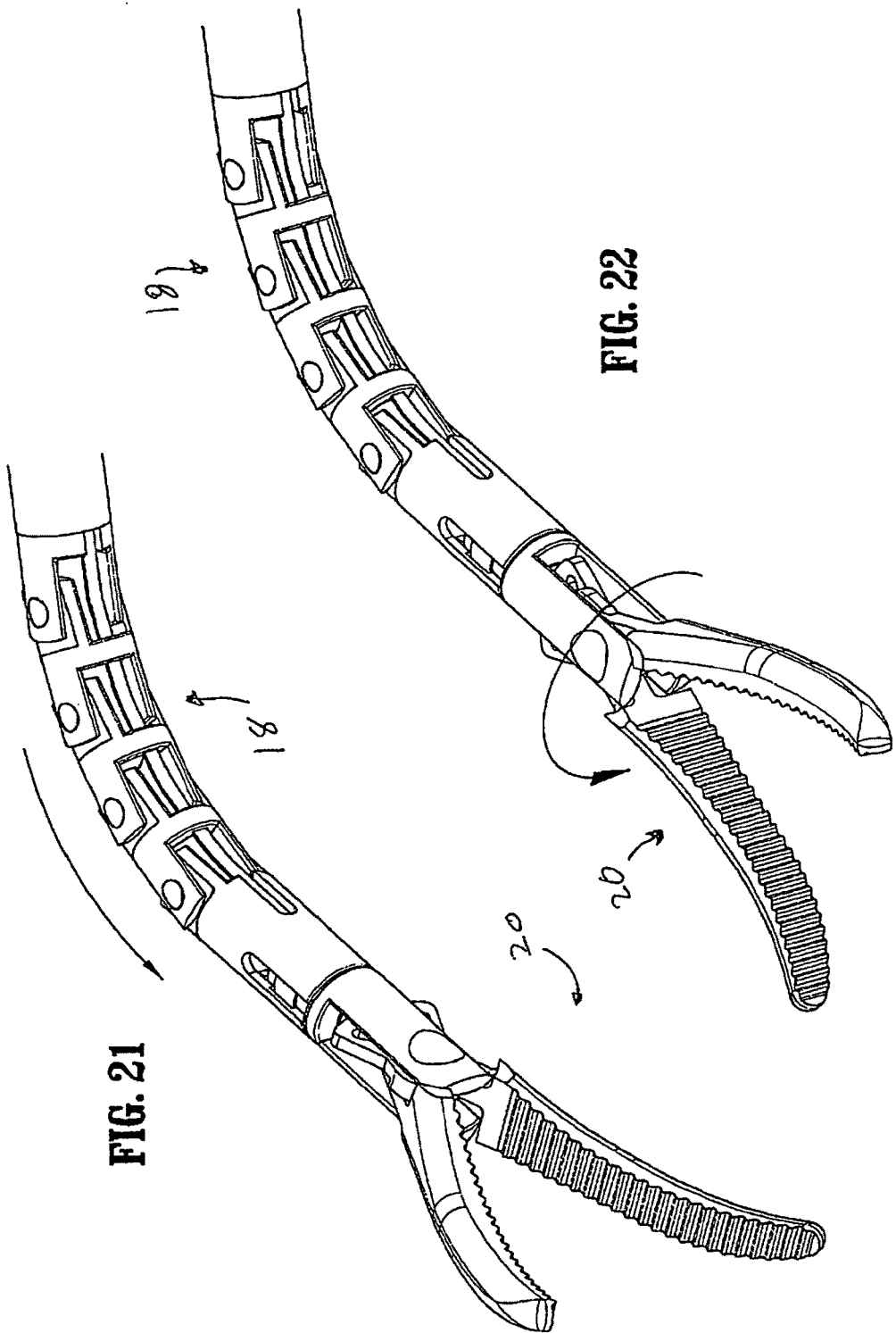

ARTICULATING SURGICAL INSTRUMENT

CROSS-REFERENCE TO RELATED APPLICATIONS

This application claims the benefit of and priority to U.S. Provisional Patent Application No. 60/976,882, filed Oct. 2, 2007, the entire disclosure of which is incorporated by reference herein.

BACKGROUND

1. Technical Field

The present disclosure relates to an articulating surgical instrument. More particularly, the present disclosure relates to a compact, articulating surgical instrument having rotational, articulating and end effector or tip rotation functions operable by a single hand of the user.

2. Background of Related Art

During various endoscopic or laparoscopic surgical procedures it is often desirable, or even necessary, to orient the distal end of the surgical instrument being used relative to the surgical site within the body of a patient. This is typically accomplished remotely and may include bending or articulating a portion of the distal end of the surgical instrument within the body of the patient. Other reorienting methods may include rotating the entire distal end of the surgical instrument relative to a handle of the surgical instrument or rotating only the tip portion or end effector of the instrument relative to the remainder of the surgical instrument.

Various structures and/or mechanisms may be provided in the surgical instrument to perform the articulation or rotational functions. These mechanisms are often complex and bulky such that attempts to incorporate two or more functions within a single surgical instrument result in an instrument which is unwieldy and requires both hands of the user to operate.

Thus, it would be desirable to provide a surgical instrument having articulation and various rotational functions within a compact package suitable for use with various end effector assemblies. It would further be desirable to provide a surgical instrument having articulation and various rotational functions in an ergonomic package operable by a single hand of the user.

SUMMARY

There is provided a surgical instrument including a handle and an elongate tubular member extending distally from the handle and having an articulating section bendable relative to the remainder of the elongate tubular member. An articulating mechanism is provided for bending the articulating section, the articulating mechanism including a flexible band and a rotatable wheel mounted on the handle and engagable with the flexible band such that rotation of the wheel relative to the handle translates the band. Translational movement of the flexible band moves the articulation section from a first neutral position to a second bent position.

The articulating mechanism includes a shuttle transferring the rotational motion of the wheel to linear motion in the band. The wheel has a groove and the shuttle is engagable with the groove. The shuttle includes a pin movable within the groove in the wheel.

In one embodiment, the groove is in the form of a spiral. In a more specific embodiment, the spiral groove is in the form of an Archimedes spiral.

The articulating mechanism also includes a collar affixed to a proximal end of the band, the collar being engagable by the shuttle. The collar is engagable by a hook on the distal end of the shuttle and is free to rotate relative to the shuttle. In one embodiment, the articulation mechanism includes a first and a second band, the first and second bands being engagable with respective first and second grooves formed in opposed sides of the wheel. The articulation mechanism further includes first and second shuttles such that proximal ends of the first and second shuttles are engagble with the respective first and second grooves in the wheel.

In a specific embodiment, the first and second grooves are oriented in reverse directions on opposed sides of the wheel. The articulation mechanism also includes first and second collars affixed to proximal ends of the first and second bands. The first and second collars are engagable with the first and second shuttles such that rotation of the wheel reciprocates the first and second bands.

DESCRIPTION OF THE DRAWINGS

An embodiment of the presently disclosed articulating surgical instrument is disclosed herein with reference to the drawings, wherein:

FIG. 5a is a perspective view, similar to FIG. 5, with several internal components removed;

FIG. 5b is an enlarged area of detail view of a collar of the articulating section of the articulating surgical instrument;

FIG. 13 is a top view of the articulation mechanism in a first position;

FIG. 14 is a top view of the articulation mechanism in a second position;

FIG. 15 is a top view of the articulating section in a neutral position;

FIG. 16 is a top view of the articulating section in an articulated position;

FIG. 16c is a top view, partially shown in section, of the elongate tubular member and end effector components in a neutral position;

FIG. 16d is a top view, similar to FIG. 16c, in an articulated position;

FIG. 18a is a perspective view of the distal end of the articulating surgical instrument in a neutral position;

FIG. 18b is a perspective view, similar to FIG. 18a illustrating rotation of the distal end of the articulating surgical instrument;

FIG. 21 is a perspective view of the elongate tubular member in an articulated position; and FIG. 22 is a perspective view of the elongate tubular member in an articulated position and the end effector assembly in a rotated position relative to the elongate tubular member.

DETAILED DESCRIPTION

An embodiment of the presently disclosed articulating surgical instrument will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
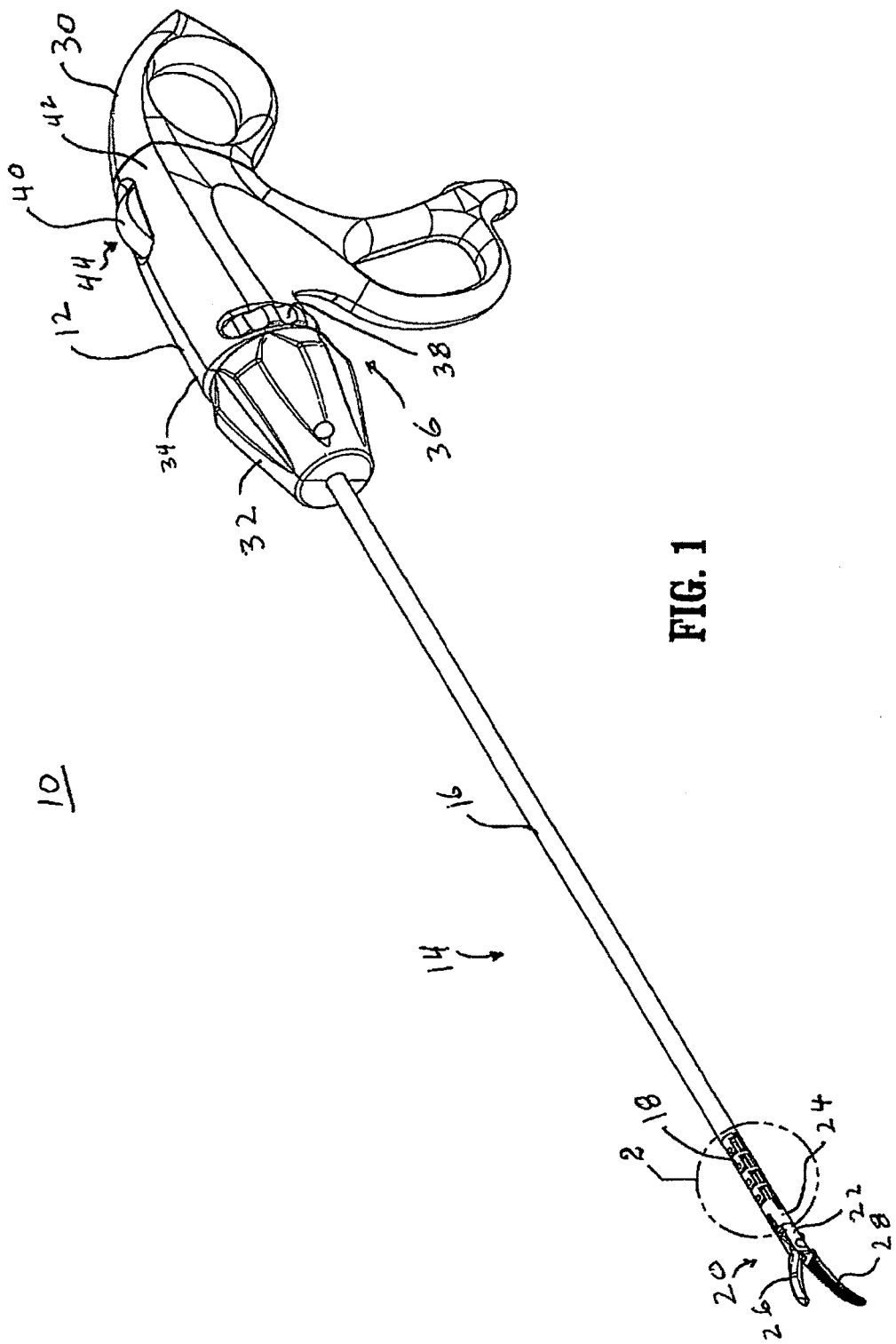
FIG. 1 is a perspective view of the disclosed articulating surgical instrument.

Referring to FIG. 1, an articulating surgical instrument or surgical instrument 10 is provided to allow single handed operation of actuation, articulation and various rotation functions and generally includes a handle 12 having an elongate tubular member 14 extending distally from handle 12. Elongate tubular member 14 includes an outer tube 16 and an articulating section 18 extending distally from outer tube 16. An end effector assembly 20 extends distally from articulating section 18 and includes a clevis or yoke 22 mounted to a distal most link 24 of articulating section 18. A first jaw 26 and a second jaw 28 are movably mounted on yoke 22 and are movable from an open position spaced apart from each other to a closed substantially adjacent one another and provide various cutting, grasping, functions, etc. A trigger 30 is movably mounted on fixed handle 12 and is operable to move first and second jaws 26 and 28, respectively, between the open and closed positions.

As noted above, surgical instrument 10 is ergonomically configured to allow single handed operation of the various actuation, articulation and rotational functions. A rotation knob 32 is provided on a distal end 34 of handle 12 and is operable to rotate the entire elongate tubular member 14 and end effector assembly 20. However, in some instances it is desirable to just rotate end effector assembly 20 relative to the remainder of surgical instrument 10. Thus, surgical instrument 10 is provided with a roticulation assembly 36 which is capable of rotating just end effector assembly 20 relative to elongate tubular member 14 regardless of whether articulation section 18 of elongate tubular member 14 is in a neutral or articulated position. Roticulation assembly 36 includes a reticulation wheel 38, provided centrally on fixed handle 12 and operable by a finger of the user, to effect rotation of end effector assembly 20. Wheel 38 extends transversely through handle 12 and exits both sides of handle 12 so as to be operable by the index finger of the user regardless of which hand is used to operate surgical instrument 10.

Surgical instrument 10 is provided with an articulation wheel 40, located at a proximal end 42 of handle 12, which is operable by a finger of the user to move articulation section 18 between the neutral and articulated positions. Articulation wheel 40 is oriented in longitudinal alignment with handle 12 to be easily operated by the thumb of the user. Articulation wheel 40 forms part of an articulation assembly 44 as discussed in more detail herein below.

Figure 2:
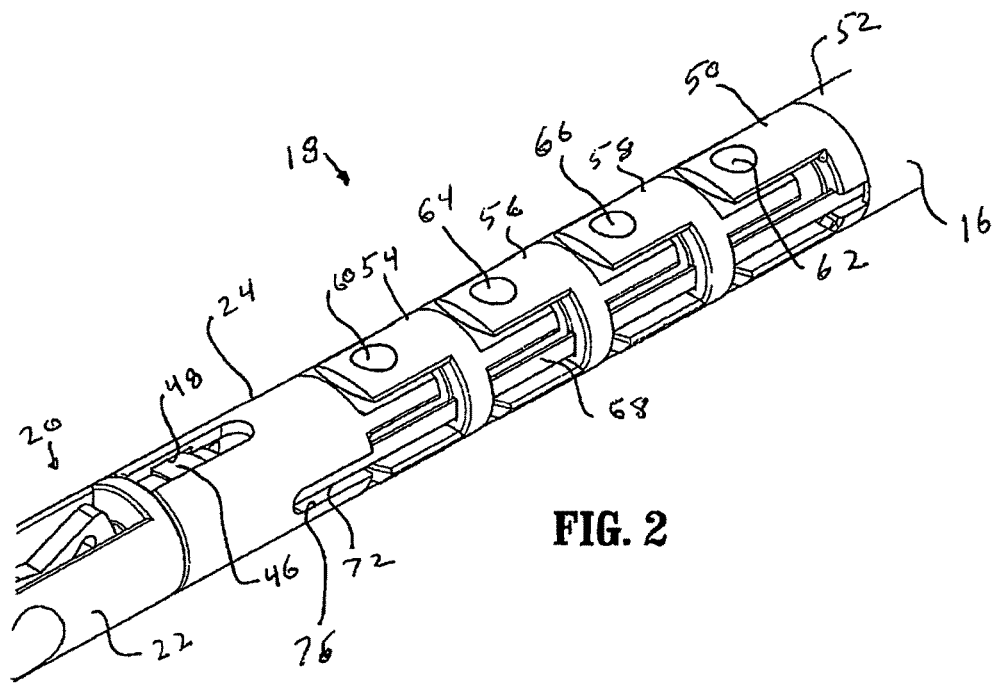
FIG. 2 is one perspective view of an articulating section of the articulating surgical instrument.
Figure 3:
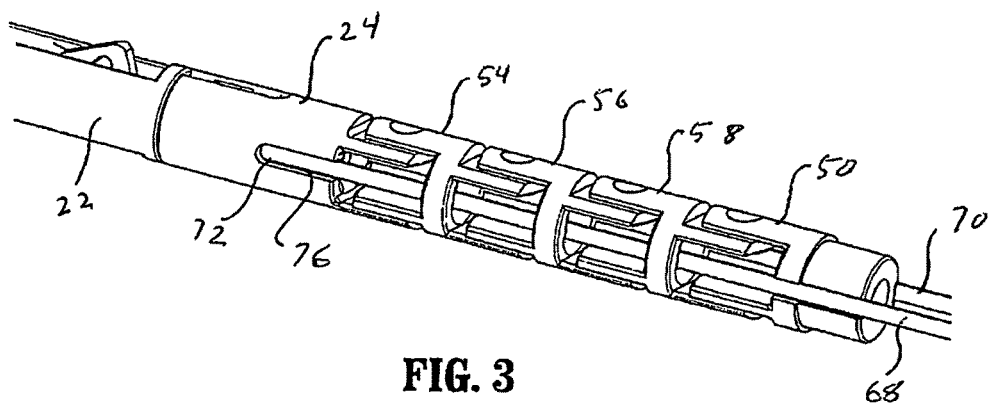
FIG. 3 is another perspective view of the articulating section of the articulating surgical instrument.

Referring now to FIGS. 2 and 3, and initially with respect to FIG. 2, as noted above, end effector assembly 20 is rotatable relative to the remainder of surgical instrument 10. Specifically, yoke 22 of end effector assembly 20 includes a collar 46 which is rotatably supported within a groove 48 formed within distalmost link 24 of articulating section 18. With further reference to FIG. 2, a proximalmost link 50 of articulating section 18 is affixed to a distal end 52 of outer tube 16. Articulating section 18 includes at least one intermediate link and, in this embodiment, includes a plurality of intermediate links 52, 54 and 56. Intermediate link 52 is connected to distalmost link 24 by a pin 60. Similarly, proximalmost link 50 is connected to intermediate link 56 by a pin 62. Intermediate link 52 is connected to intermediate link 54 by a pin 64 and intermediate link 54 it is connected to intermediate link 56 by a pin 66. By connecting the disclosed links with a series of pins, the links of articulating section 18 may bend or flex in a single plane to orient end effector assembly 20 relative to outer tube 16. The specific structural details of the intermediate links and associated pins are described in more detail herein below.

In order to bend or flex the links about the respective pins, articulation assembly 44 is provided with a pair of longitudinally extending and reciprocating bands 68 and 70 which extend from distalmost link 24 proximally through links 54, 56, 58 and 50 of articulating section 18 and through outer tube 16. Bands 68 and 70 extend into handle 12 where they are operatively associated with articulation wheel 40. Advancement of one of bands 68 or 70 and simultaneous retraction of the other of bands 68 or 70 function to cause links 24, 52, 54, 56 and 50 to bend relative to each other thereby causing a bend in articulating section 18. Distal ends 72 and 74 of bands 68 and 70 are affixed within slots 76 and 78, respectively, formed in distalmost link 24.

Figure 4:
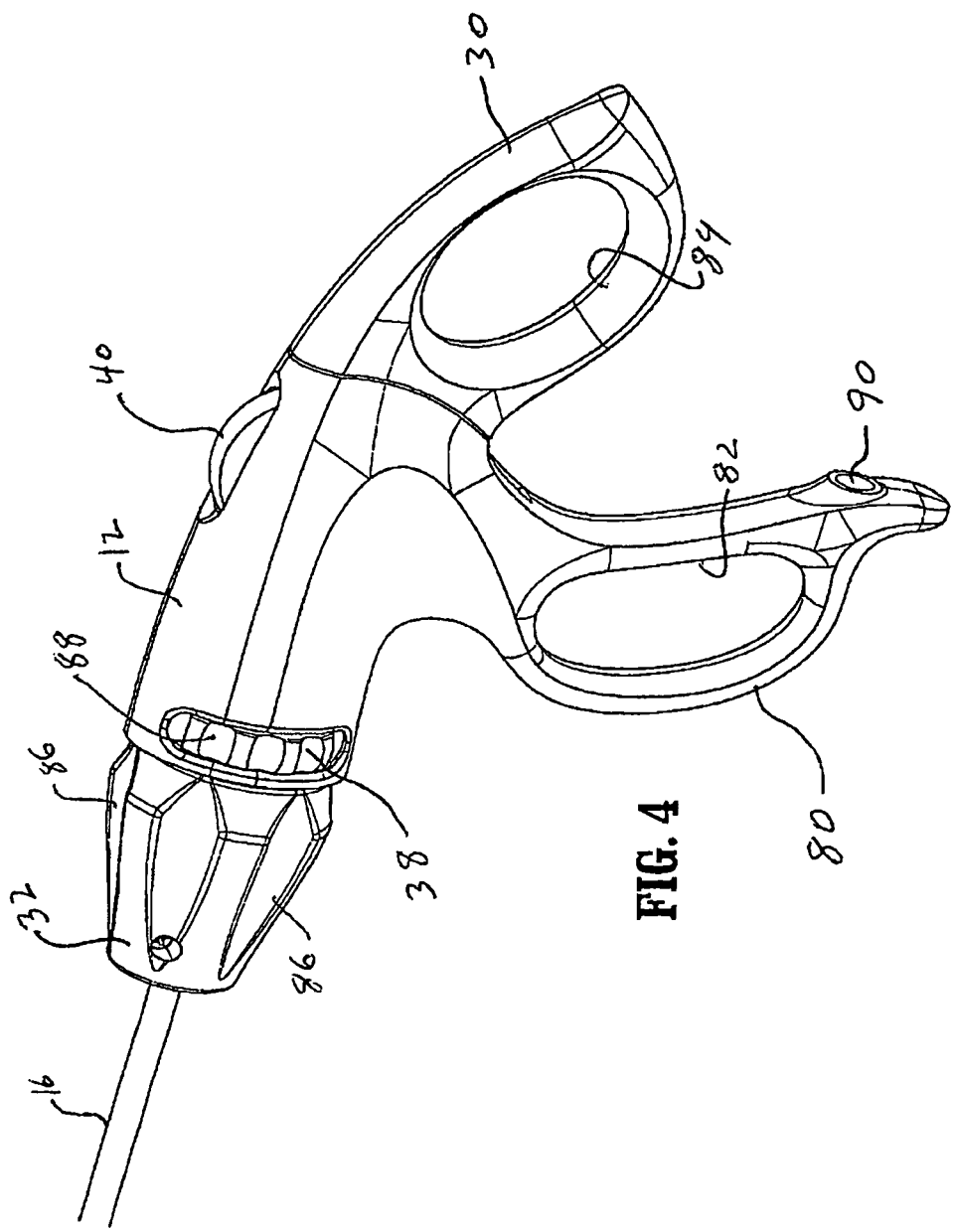
FIG. 4 is perspective view of a handle portion of the articulating surgical instrument.

Referring now to FIG. 4, and as noted hereinabove, surgical instrument 10 is specifically configured and ergonomically engineered for operation by a single hand of the user. Thus, pistol grip handle 12 has a depending portion 80 which forms a finger loop 82 for receipt of the fingers of the operator. Similarly, trigger 30 forms a trigger or thumb loop 84 for receipt of the thumb of the user in order to actuate end effector assembly 20. As shown, roticulation wheel 38 is positioned intermediate rotation knob 32 and articulation wheel 40. The user may use the index finger in order to operate rotation knob 32 and\or reticulation wheel 38. Articulation wheel 40 may be operated by the thumb of the user. In order to facilitate engagement by the fingers of the user, rotation knob 32 is provided with a series of longitudinally extending flutes 86. Further, reticulation wheel 38 is provided with a series of ribs 88 to facilitate engagement with the finger at the user. While not specifically shown, articulation wheel 40 may be likewise textured, grooved or fluted to facilitate engagement by the thumb of the user.

In some embodiments of surgical instrument 10 it may be useful to provide electro-cautery, light, etc. functions to surgical instrument 10. Thus, handle 12, and specifically depending portion 80 may be provided with a power port 90 for receipt of a power or optical source.

Figure 5:
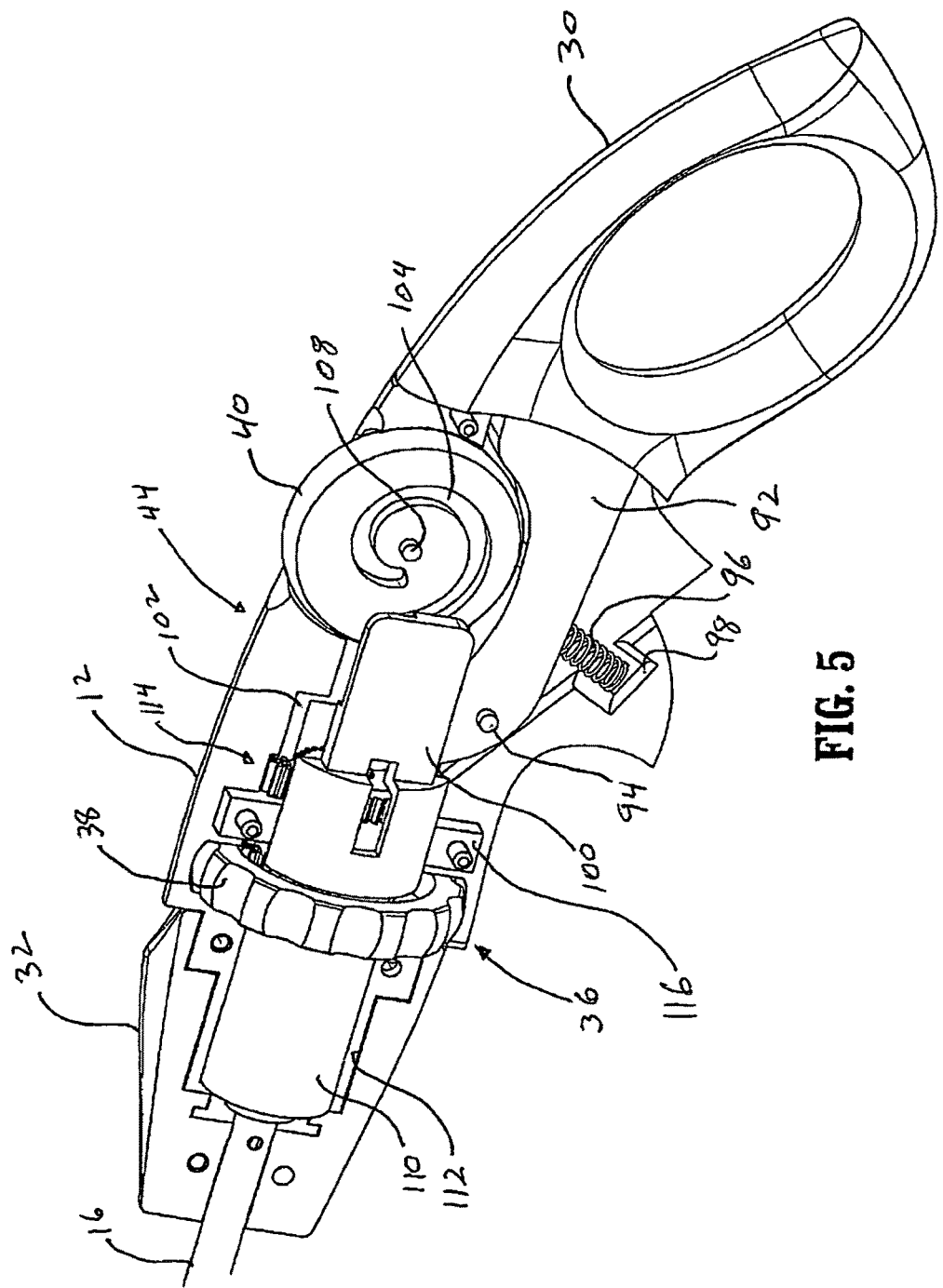
FIG. 5 is a perspective view, with half a handle housing removed, of the handle portion of the articulating surgical instrument.

Referring now to FIG. 5, surgical instrument 10 is illustrated with half of handle 12 removed. As noted above, trigger 30 is movable relative to handle 12. Trigger 30 includes a longitudinally extending trigger arm 92 which is pivotally mounted on a trigger pin 94 formed in handle 12. A spring 96 is provided to bias trigger 30 relative to handle 12 and is positioned between trigger arm 92 and a trigger recess 98 formed in handle 12.

Articulation assembly 44 includes a first shuttle 100 and a second shuttle 102 which are engageable with articulation wheel 40 and remotely engageable with bands 68 and 70 to effect bending of articulating section 18. Articulation wheel 40 is provided with a pair of grooves 104 and 106 (not shown) on opposite sides of articulation wheel 40 and which are configured to be engaged by first and second shuttles 100 and 102, respectively. Specifically, first and second shuttles 100 and 102 are supported for longitudinal movement within handle 12. Rotation of articulation wheel 40 effects longitudinal movement of first shuttle 102 and second shuttle 102 in a manner described in more detail hereinbelow.

As noted hereinabove, reticulation assembly 36 includes a roticulation knob 38. Roticulation knob 38 includes a longitudinal tube 110 positioned within a handle recess 112. Longitudinal tube 110 rotatably supports reticulation knob 38 relative to handle 12. Roticulation assembly 36 further includes a gear train 114 engageable with roticulation knob 38 to facilitate rotation of end effector assembly 20. Gear train 114 is supported within handle 12 by a bracket 116.

Figure 6:
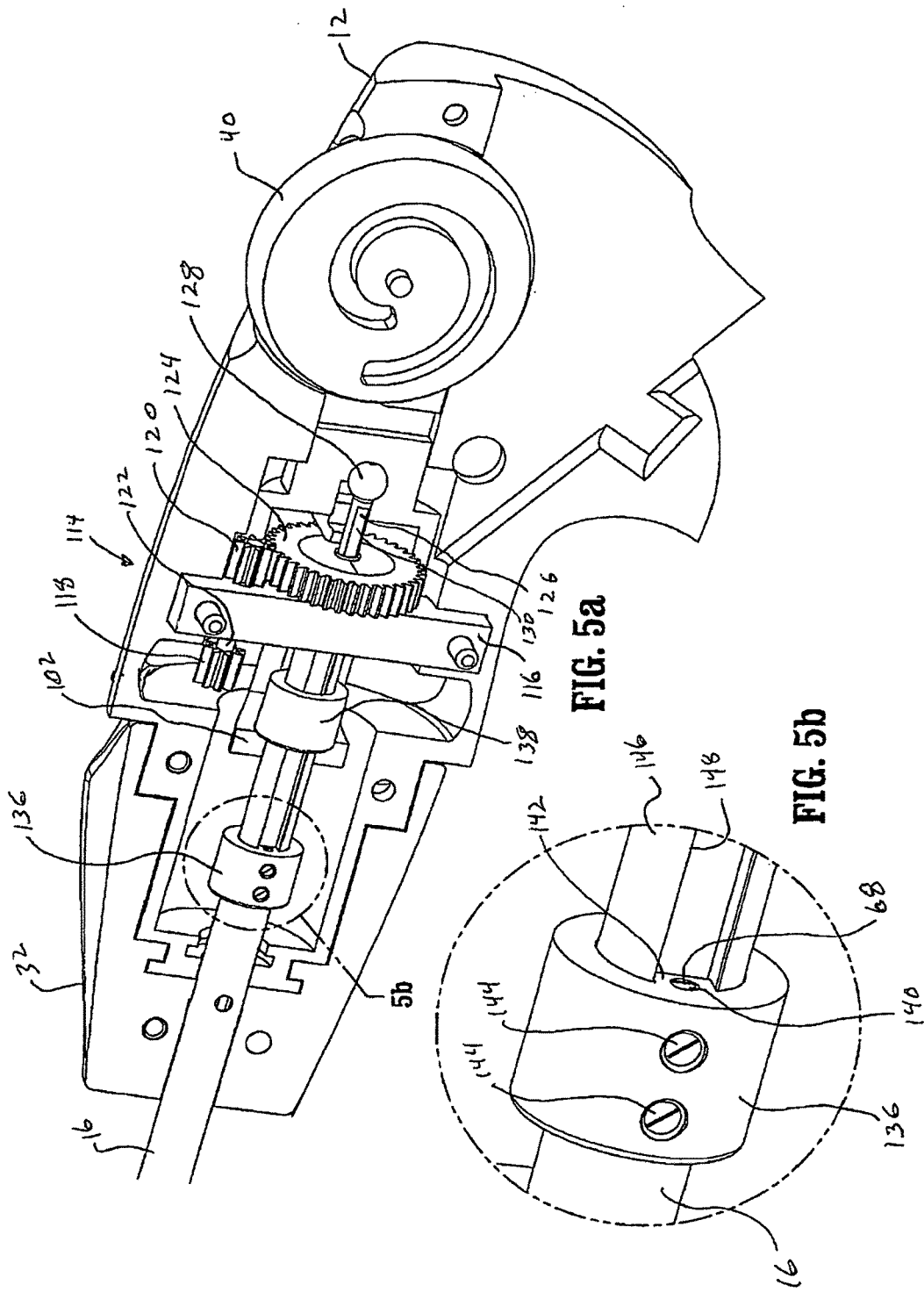
FIG. 6 is a side view, shown in section, of the handle portion of the articulating surgical instrument.

Referring to FIGS. 5a and 6, gear train 114 includes a first transfer gear 118 and a second transfer gear 120. First and second transfer gears 118 and 120 are interconnected by a transfer shaft 122. Transfer shaft 122 is rotatably supported within handle 12 by bracket 116. First transfer gear 118 is engageable with roticulation wheel 38 while second transfer gear 120 is engageable with a reticulation gear 124. A drive rod 126 is mounted within handle 12 and includes a ball end 128 and a keyed shaft 130 extending distally from ball end 128. Keyed shaft 130 extends through reticulation gear 124 such that keyed shaft 130 engages and rotates with roticulation gear 124. Keyed shaft 130 is also longitudinally movable through reticulation gear 124 to operate and effector assembly 20.

Figure 7:
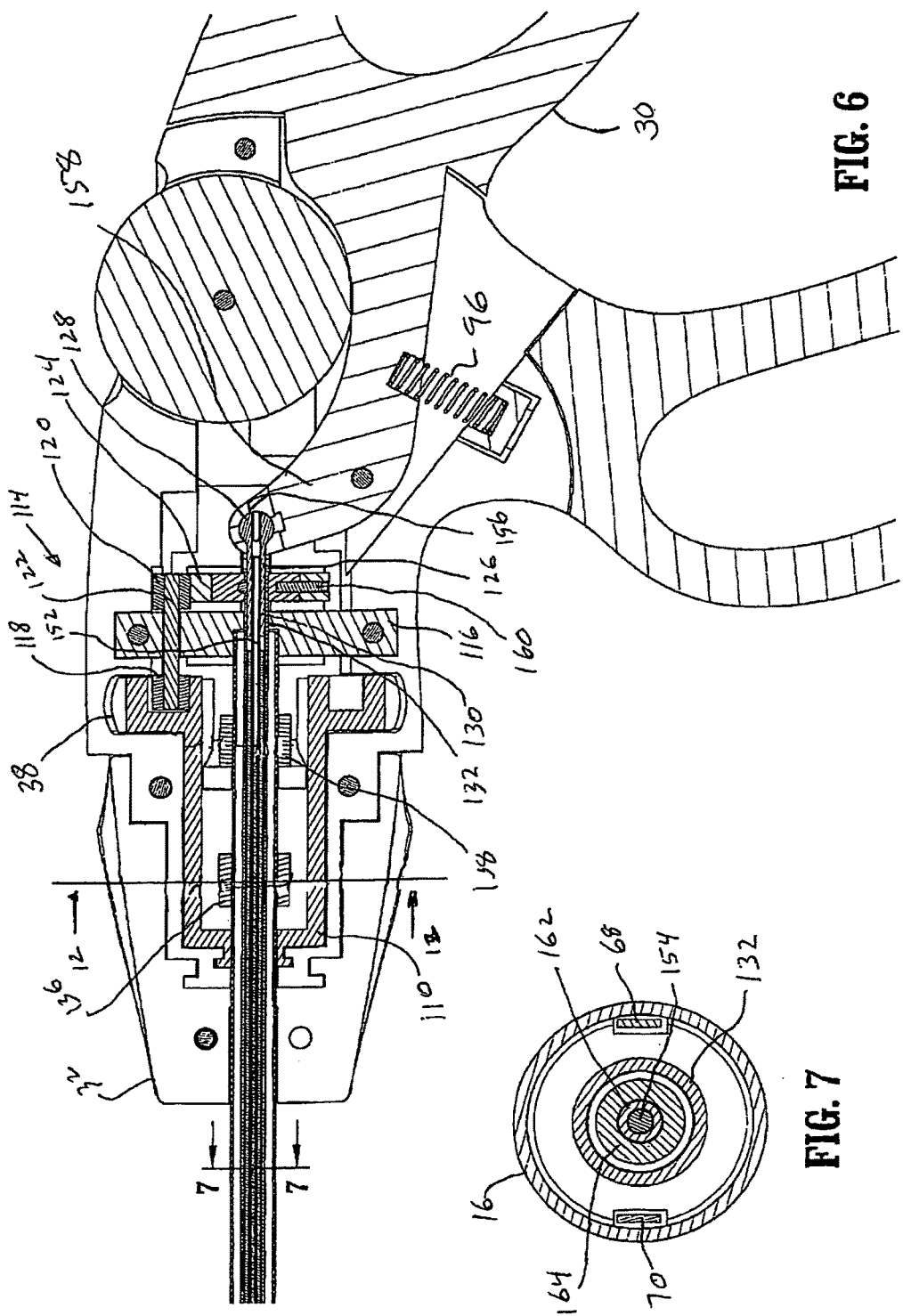
FIG. 7 is a cross-sectional view, taken along line 7-7, of FIG. 6.

Referring to FIGS. 6 and 7, keyed shaft 130 also engages, and rotates with, a reticulation tube 132 which extends through elongate tubular member 14 to end effector assembly 20.

Referring back to FIG. 5a, in order to enable first and second shuttles 100,102 to move bands 68 and 70, articulation assembly 44 additionally includes a first band collar 136 and a second band collar 138. First and second band collars 136 and 138 are configured to receive first and second bands 68 and 70, respectively, and be engaged by first and second shuttles 100 and 102.

As best shown in FIG. 5b, band 68 is secured within a bore 140 provided in first band collar 136 by a pair of set screws 144. Specifically, bore 140 is formed in an inwardly directed projection 142 of first band collar 136. As also shown, a proximal end 146 of outer tube 16 is formed with a pair of slots 148 and 150 (not shown). Projection 142 of first band collar 136 rides within slot 148 such that first band collar 136 may move longitudinally along outer tube 16 while at the same time rotate simultaneously with rotation of outer tube 16. This allows band 68 of articulation mechanism 44 to move longitudinally relative to outer tube 16 to bend articulation section 18. Additionally, by rotating band 68 with rotation of outer tube 16, twisting of band 68 relative to outer tube 16 is prevented. While not specifically shown, second band collar 138, including second band 70, engages slot 150 of outer tube 16 and functions similar to that described with respect to first band collar 136 in order to advance and retract second band 70 relative to outer tube 16.

Referring to FIG. 6, as noted above, trigger 30 is provided to operate end effector assembly 20. Drive rod 126 is connected to a proximal end 152 of a flexible center rod 154 (FIG. 7). In order to move drive rod 126 longitudinally within handle 12, ball end 128 of drive rod 126 is positioned within a trigger receptacle 156 formed in a distal end 158 of trigger arm 92. Thus, as trigger 30 is moved against the bias of spring 96, ball end 128 of drive rod 126, and thus center rod 154, is drawn proximally within elongate tubular member 14 to actuate end effector assembly 20 as described in more detail herein below.

As best shown in FIG. 6, roticulation gear 124 is secured to reticulation tube 132 by a set screw such that, as roticulation gear 124 is rotated by reticulation wheel 38, reticulation tube 132 is also rotated to rotate end effector assembly 20 independent of elongate tubular member 14 in a manner described in more detail herein below.

Referring now to FIG. 7, the nesting of the various components within outer tube 16 will now be described. Articulation bands 68 and 70 pass along the inside of outer tube 16. Center rod 154 passes down the center of outer tube 16 while roticulation tube 132 is positioned between center rod 154 and the inside of outer tube 16. A flexible jaw cable tube 162 may be provided around center rod 154 and guide center rod 154 during its longitudinal motion through outer tube 16 as well as through articulation section 18. In the event that surgical instrument 10 incorporates electrocautery features, a jaw cable insulation 164 may be provided around jaw cable tube to insulate the remainder of surgical instrument 10 from current applied to end effector assembly 20 through center rod 154.

Figure 8:
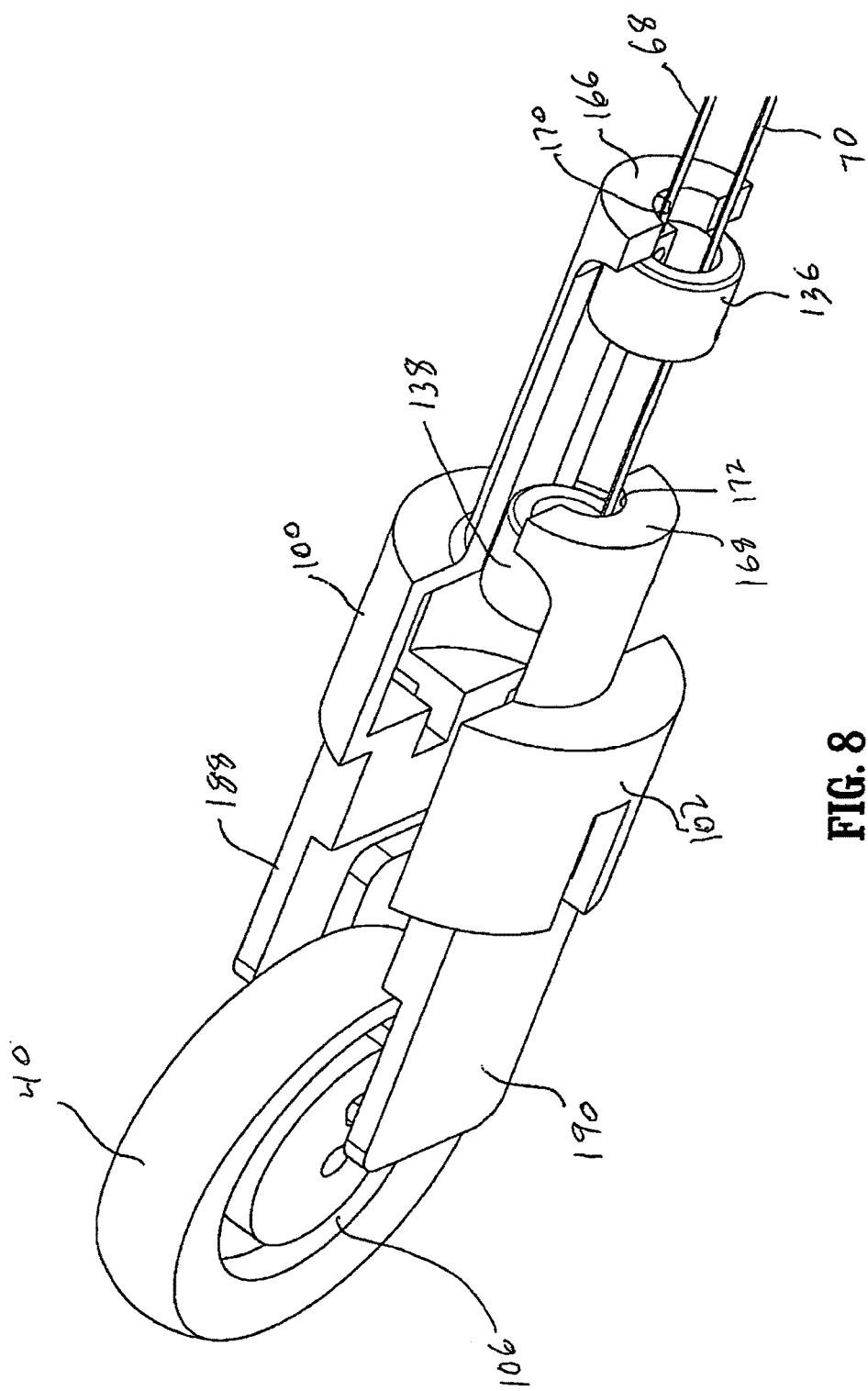
FIG. 8 is a perspective view of an articulation mechanism of the articulating surgical instrument.
Figure 9:
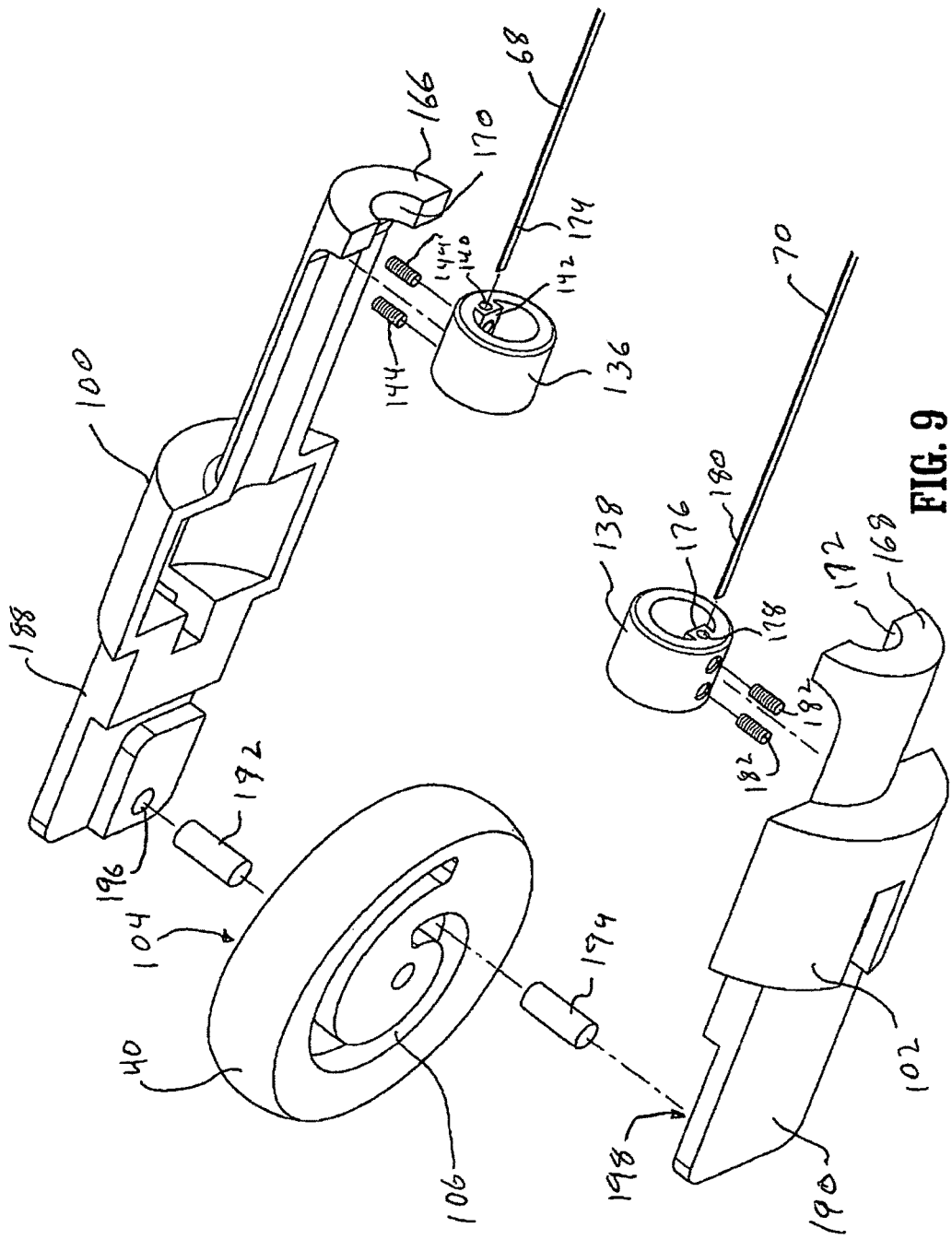
FIG. 9 is a perspective view of the articulation mechanism with parts separated.

Referring now to FIGS. 8-16b, and initially to FIGS. 8 and 9, the assembled components and function of articulation assembly 44 will now be described independent of the remaining rotational functions. As noted hereinabove, shuttles 100 and 102 are provided to advance and retract first and second band collars 136 and 138, respectively, within handle 12. Shuttles 100 and 102 are provided with distal hooks 166 and 168 which engage and alternatively retract first and second band collars 136 and 138. Hooks 166 and 168 are provided with respective circular cutouts 170 and 172 to accommodate the passage of proximal end 146 of outer tube 16 therethrough. As noted above, first band collar 136 includes bore 140 for receipt of proximal end 174 of first band 68. Set screws 144 secure first band 68 within bore 140. Similarly, second band collar 138 includes an inward projection 176 having a bore 178 for receipt of proximal end 180 of second band 70. Set screws 182 are provided to secure proximal end 180 within bore 178.

As best shown in FIG. 9, first and second shuttles 100 and 102 include central recesses or cavities 184 and 186 to accommodate reticulation gear 124. It should be noted that this, along with gear train 114 of roticulation assembly 36, allows for multiple articulation and rotational functions within a compact and ergonomically designed handle 12 by minimizing the space needed by each function within handle 12.

Shuttles 100 and 102 have respective proximal ends 188 and 190 which are configured to engage articulation wheel 40 and, along with grooves 104 and 106, translate rotational motion of articulation wheel 40 into longitudinal and reciprocal motion of shuttles 100 and 102. Shuttles 100 and 102 are provided with respective pins 192 and 194 which ride within grooves 104 and 106, respectively. Pin 192 is positioned within a recess 196 in first shuttle 100 and pin 194 is positioned within a recess 198 in second shuttle 102.

It should be noted that, since first and second bands 68 and 70 are secured to distal most link 24 (FIGS. 2, 3 and 16*b*), as one of bands 68 or 70 is pulled proximally by respective hook 166 or 168 the other of bands 68 or 70 is automatically drawn distally. Thus, there is no need on shuttles 100 and 102 for the provision of a structure for pushing or driving either of the collars distally.

Figure 10:
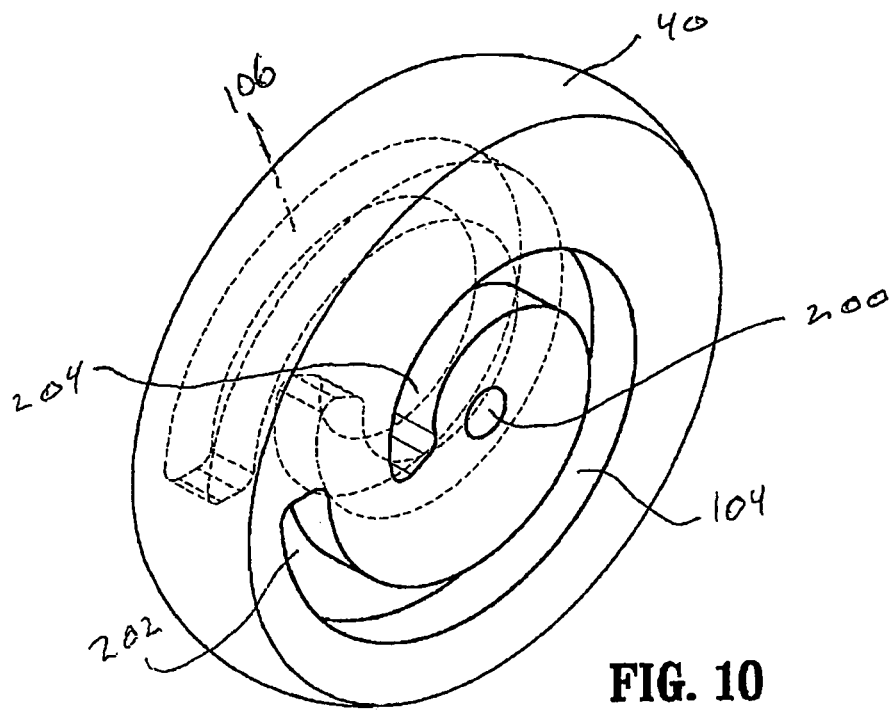
FIG. 10 is perspective view of an articulation wheel of the articulating surgical instrument.
Figure 11:
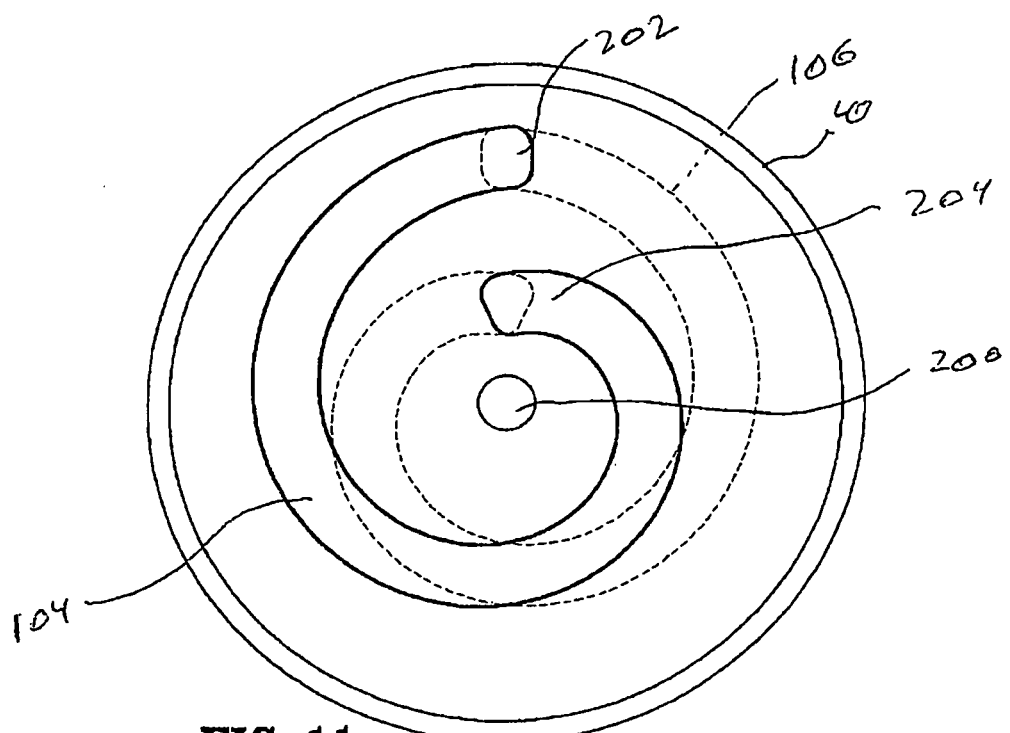
FIG. 11 is a side view of the articulation wheel.

Referring now to FIGS. 10 and 11, and as noted above, articulation wheel 40 is provided with grooves 104 and 106 located on opposite sides of articulation wheel 40. Grooves 104 and 106 are mirror images of each other and are oriented in reverse directions. Pins 192 and 194 positioned within grooves 104 and 106 move in opposite directions, i.e., one distally and one proximally, as articulation wheel 40 is rotated. Since pins 192 and 194 are constrained by shuttles 100 and 102, pins 192 and 194 are restricted to linear motion within handle 12. Using groove 104 as an example, articulation wheel rotates about a central pivot hole 200 (which is used to mount articulation wheel 40 on wheel pin 108 on handle 12, See FIG. 5). A first end 202 of groove 104 is located furthest away from pivot hole 200 while a second end 204 is located closest to pivot hole 200. As pin 192 (not show) moves within groove 104 it travels linearly between first end 202, corresponding to a distal most position of pin 192 and thus shuttle 100, and second end 204 corresponding to a proximal most position of pin 192 and thus shuttle 100.

Advantageously, both grooves 104 and 106 are in the form of Archimedes spirals which allow for this translation of rotational to linear motion. The use of Archimedes spirals with accelerated radii of curvature also provides differential torque to pins 192,194 so as to prevent pins 192,194 from sticking or becoming jammed within grooves 104 and 106.

Figure 12:
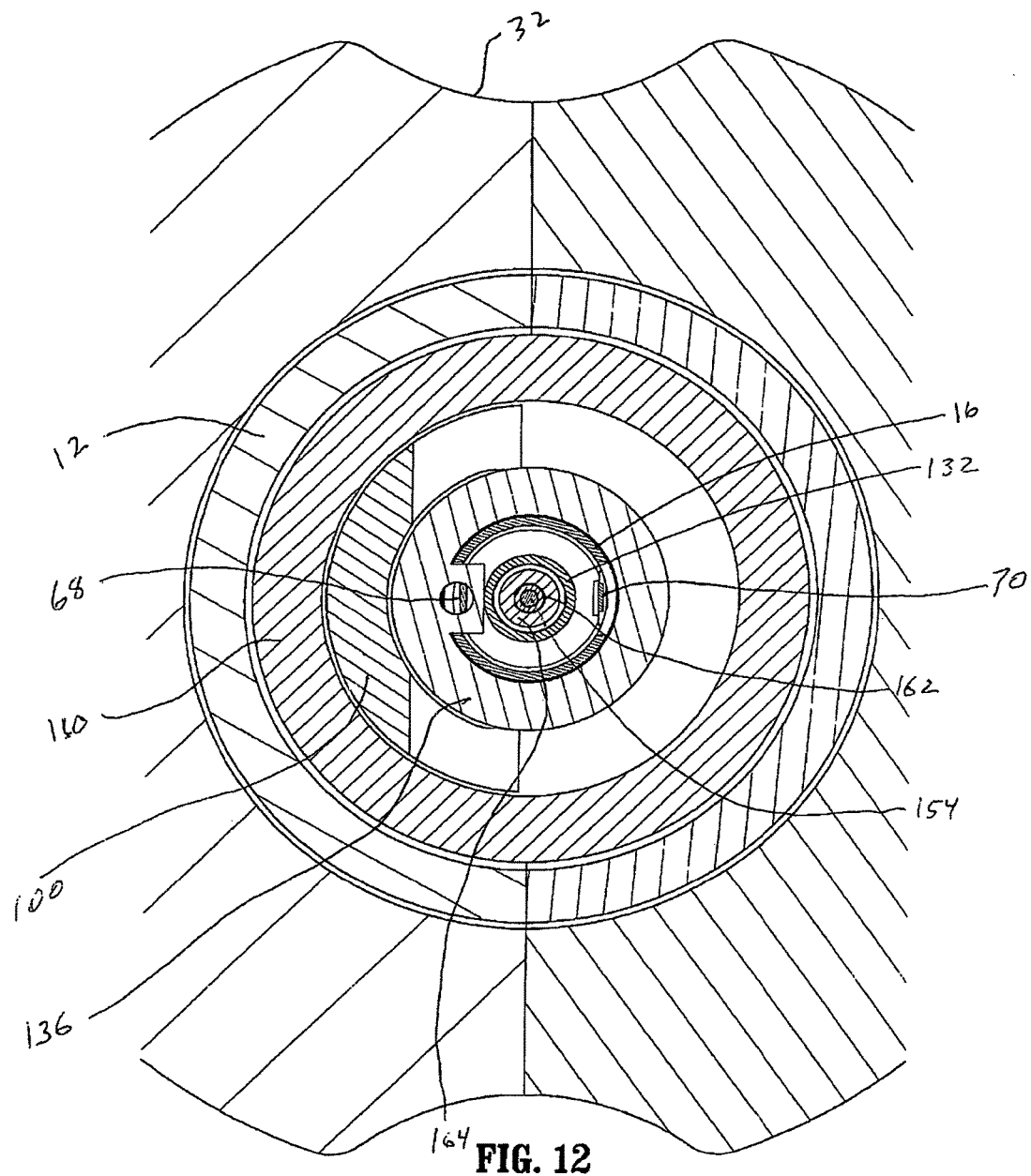
FIG. 12 is a cross-sectional view, taken along line 12-12 of FIG. 6.

Referring for the moment to FIG. 12, the nesting or compact positioning of the various components within the distal end of handle 12, beneath rotation knob 32, is illustrated. Rotation knob 32 is positioned about handle 12. Tube 110 of roticulation wheel 38 is positioned within handle 12 and first shuttle 100 is slidable therein. First band collar 100 secures first band 68 while allowing free longitudinal movement of second band 70 therethrough. First collar 100 also slides along outer tube 16. Center rod 154 is surrounded by jaw cable tube 162, and if eletrocautery is present, also by jaw cable insulation 164. Finally, reticulation tube 132 is positioned between center rod 154 and outer tube 16.

Turning now to FIGS. 13-16, and initially to FIG. 13, the operation of articulation assembly 44 will now be described. As articulation wheel is rotated in a first direction first pin 192 moves proximally within groove 104 thereby drawing first shuttle 100 proximally. Hook 166 of first shuttle 100 draws first band collar 136, and thus first band 36, proximally. As noted above, second hook 168 of second shuttle 102 exerts no driving force on second band collar 138, but allows second band collar 138, and thus second band 70, to move distally.

Referring to FIG. 14, when articulation wheel 40 is rotated in the opposite direction, second hook 168 draws second band collar 138, and thus second band 70, proximally. First hook 166 exerts no driving force on first band collar 136, and thus on first band 68, but allows it to move freely distally.

Referring to FIG. 15, in a neutral position, articulation section 18, and thus end effector assembly 20, are in longitudinal alignment with outer tube 16 (FIG. 1). First and second bands 68 and 70 are in neutral or static positions. As shown in FIG. 16, when first and second bands 68 and 70 are reciprocated by rotation of articulation wheel 40 (FIGS. 13 and 14) articulation section 18 is moved or bent within a common plane thereby reorienting end effector assembly 20 relative to outer tube 16 (not shown). In this manner, rotation of articulation wheel 40 effects articulation of articulation section 18 to orient end effector assembly 20 relative to outer tube 16.

Figure 16A:
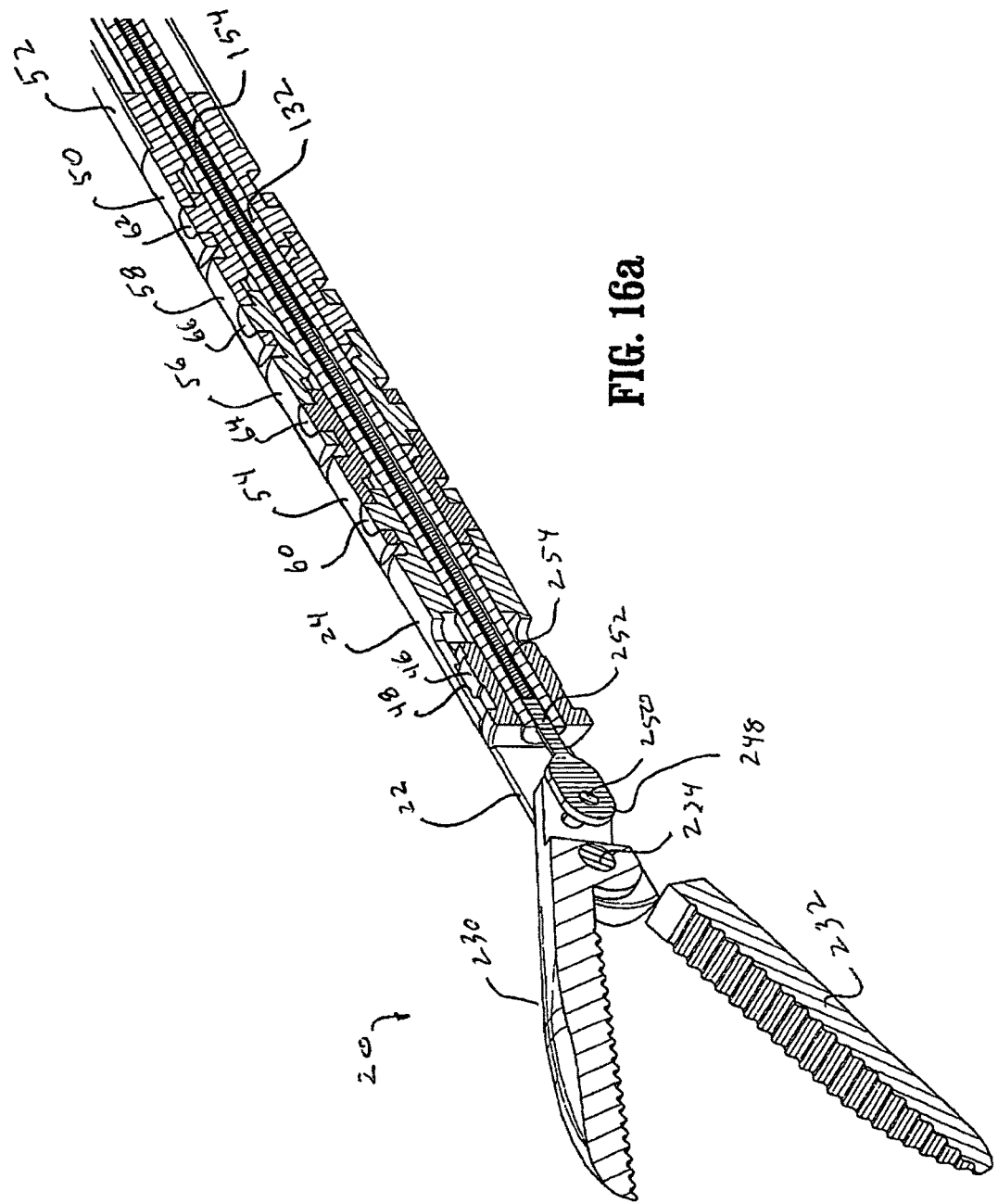
FIG. 16a is a perspective view, shown in section, of the articulating section and end effector assembly.
Figure 16B:
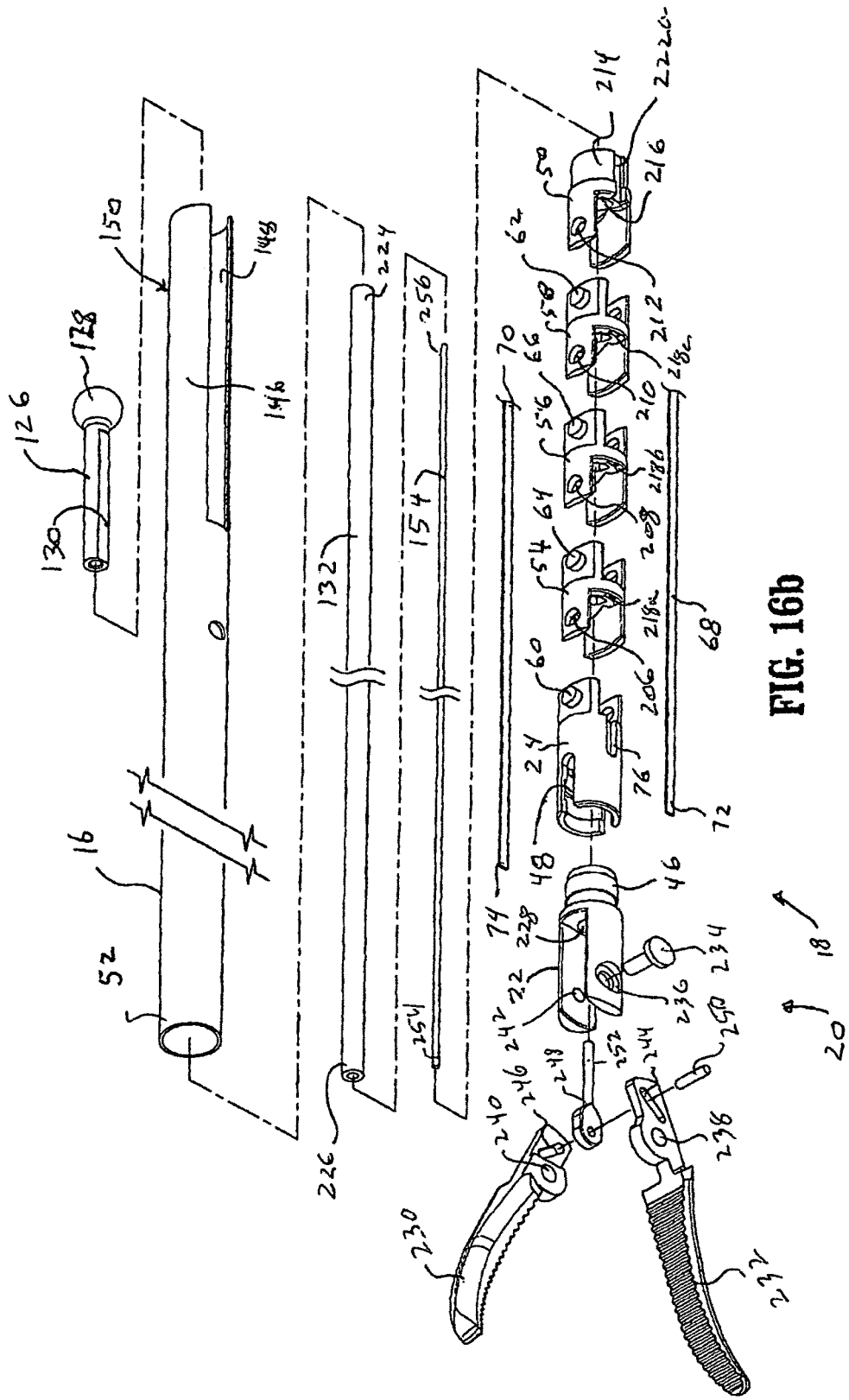
FIG. 16b is a perspective view, with parts separated, of the elongated tubular member and end effector components.

Referring now to FIGS. 16*a*-16*d*, and initially with respect to FIGS. 16*a* and 16*b*, articulation section 18 is formed from a series of links interconnected by pins that allow articulation section 18 to bend through a single plane. In the present disclosure, the pins are formed integral with the links. Pin 60 is integral to distal most link 24. Likewise, pins 62, 64 and 66 are formed integral to intermediate links 58, 54 and 56, respectively. With specific reference to FIG. 16*b*, a pin of one link is positioned within a hole formed in the next proximal link. Pin 60 on distal most link 24 is positioned within a hole 206 formed in intermediate link 54. Pin 64 on intermediate link 54 is positioned within a hole 20 in link 56 and pin 66 on link 56 is positioned within a hole 210 in link 58. Pin 62 formed in intermediate link 58 is positioned within a hole 212 formed in proximal most link 50.

With continued reference to FIG. 16*b*, proximal most link 50 includes a reduced diameter proximal portion 214 which is affixed within distal end 52 of outer tube 16. As noted hereinabove, distal ends 72 and 74 of bands 68 and 70 are affixed within slots 76 and 78 (FIGS. 16*c* and 16*d*) of distal most link 24. Band 68 slides within slots 218*a*-*c* formed within intermediate links 54, 56 and 58, respectively. Referring for the moment to FIGS. 16*c* and *d*, band 70 slides within slots 220*a*-*c* formed within intermediate links 54, 56 and 58 respectively. Bands 68 and 70 slide within grooves 222*a* and *b* formed in proximal most link 50.

A proximal end 224 of reticulation tube 132 is slidable over, and rotatable therewith, keyed shaft 130 of drive rod 126 while a distal end 226 of reticulation tube 132 is affixed within a bore 228 formed within yoke 22 of end effector assembly 20. In this manner, rotation of reticulation tube 132 rotates end effector assembly 20 independent of the remainder of surgical instrument 10.

Referring to FIGS. 16*a*-16*d*, in the present disclosure, end effector assembly 20 is a dissector such that first and second jaws 26 and 28 may be in the form of toothed first and second jaws 230 and 232, respectively, and pivotally mounted on yoke 22. Specifically, a pivot pin 234 extends through a first yoke hole 236, through pivot holes 238 and 240 formed in first and second jaws 230 and 232, and through a second yoke hole 242 formed in yoke 22. In order to open and close jaws 230,232, jaws 230 and 232 are formed with oppositely angled slots 244 and 246. A clevis 248 is provided and includes a drive pin 250 which rides within slots 244 and 246. As clevis 248 moves distally and proximally, drive pin 250 engages slots 244 and 246 to move first and second jaws 230 and 230 between an open position spaced apart from one another to a closed position substantially adjacent one another in known manner. A proximal end 252 of clevis 248 is affixed to a distal end 254 of center rod 154 such that movement of center rod 154 due to the actuation of trigger 30, as described herein above, moves clevis 248 distally and proximally to open and close jaws 230 and 232. A proximal end 256 of center rod 154 is affixed within drive rod 126.

Figure 17:
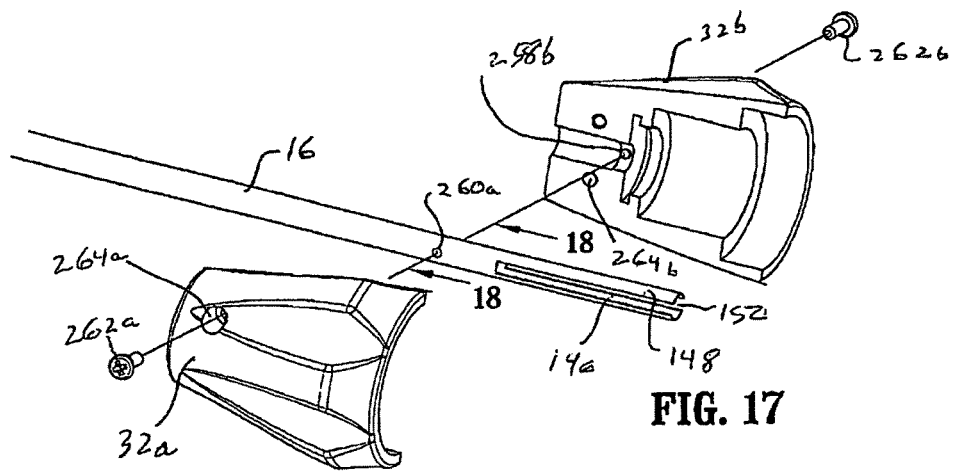
FIG. 17 is a perspective view of a proximal end of an outer tube and rotation mechanism with parts separated.
Figure 18:
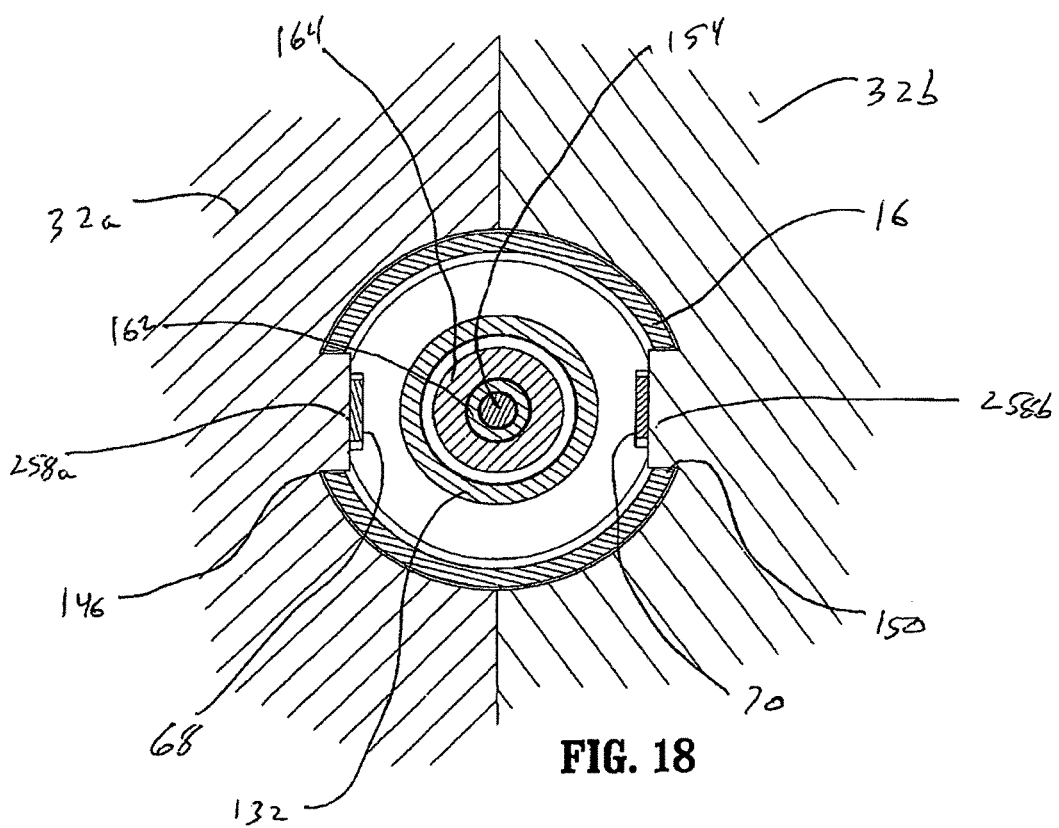
FIG. 18 is a cross-sectional view of the elongate tubular member components illustrating the connection between the rotation mechanism and the outer tube.

Referring now to FIGS. 17 and 18, and as noted above, rotation knob 32 is provided to rotate outer tube 16, and in fact the entire elongate tubular member 14 including end effector assembly 20. Rotation knob 32 is formed in halves 32a and 32b and includes respective bosses 258a and 258b which engage corresponding holes 260a and 260b in outer tube 16. A pair of screws 262a and 262b are provided to enter and engage respective holes 264a and 264b in halves 32a and 32b to secure them together about outer tube 16.

Thus, with reference to FIGS. 17, 18a and 18b, as rotation knob 32 is rotated by the index finger of the user, the entire elongate tubular member 14, including outer tube 16, articulating section 18 and end effector assembly 20, rotates from a neutral position (FIG. 18a) to a rotationally differently oriented position (FIG. 18b) as desired by the user.

Figure 19:
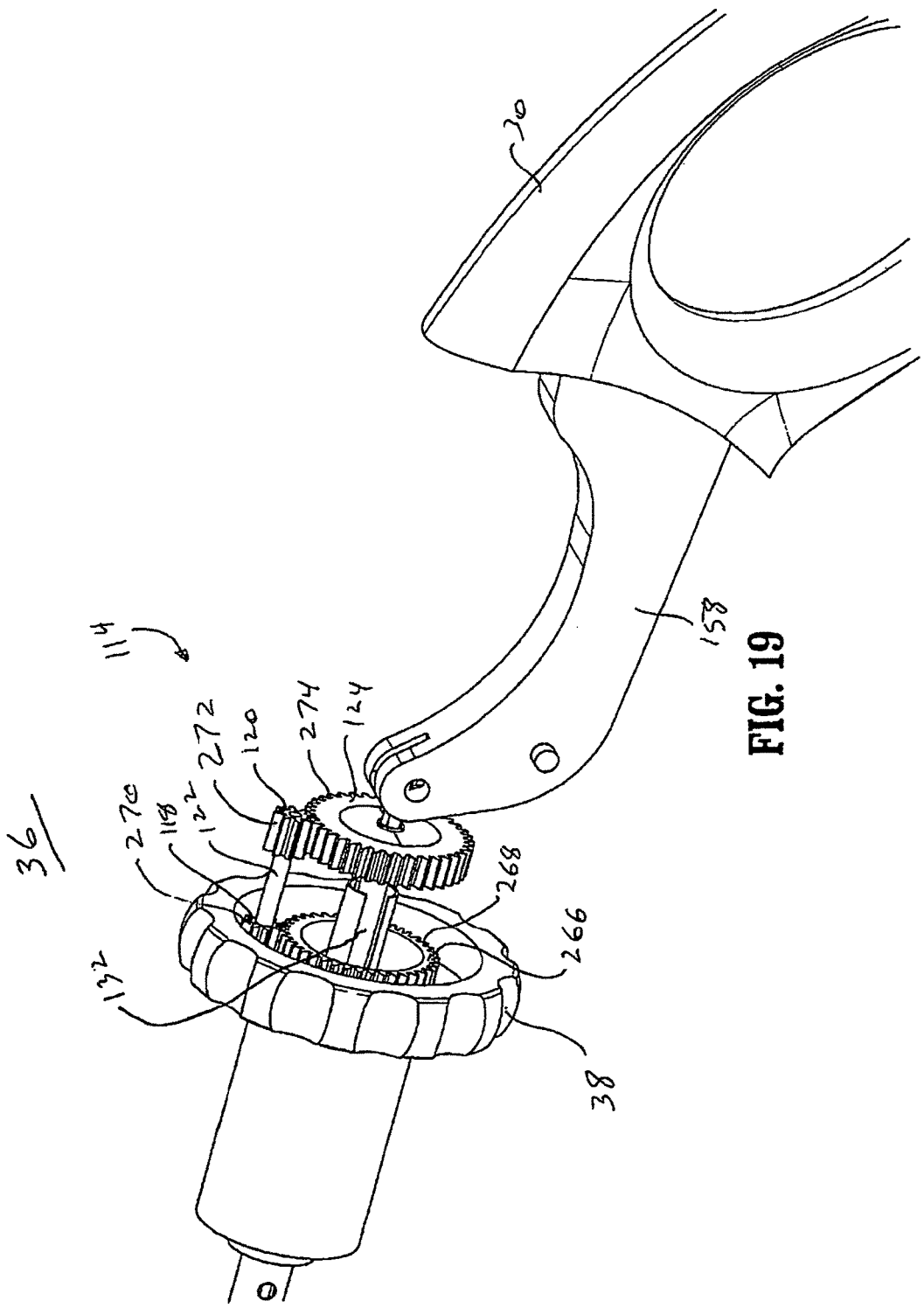
FIG. 19 is a perspective view of the reticulation mechanism of the articulating surgical instrument.
Figure 20:
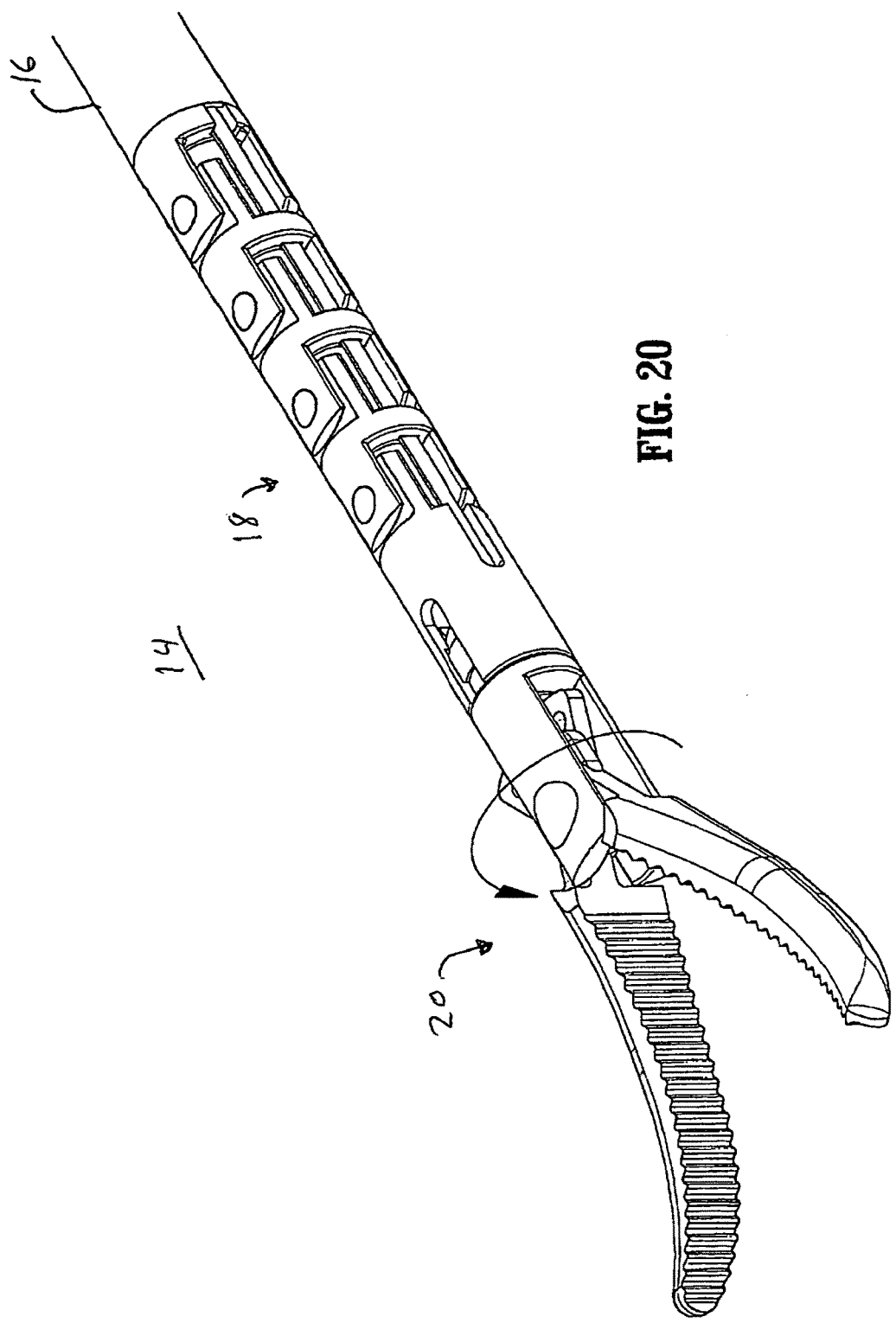
FIG. 20 is a perspective view of the distal end of the articulating surgical instrument with the end effector assembly rotated relative to the elongate tubular member.

Turning now to FIG. 19, as noted above reticulation assembly 36 is provided to rotate end effector assembly 20 (FIG. 20) independently of the remainder of surgical instrument 10. Rotation wheel 38 is provided with an inner gear 266 configured to engage gear train 114. Specifically, inner gear 266 includes gear teeth 268 which engage teeth 270 on first transfer gear 118. Likewise, second transfer gear 120 includes teeth 272 which engage teeth 274 on reticulation gear 124. As noted above, reticulation gear 124 is connected to reticulation tube 132. Thus, as reticulation wheel 32 is rotated, gear train 114 transfers the rotational motion to reticulation tube 132 to rotate end effector assembly 20 form a first or neutral position to a rotationally oriented position (FIG. 20) independently of the remainder of elongate tubular member 14.

It should be noted that gear train 114 is provided offset from reticulation tube 132 in order to provide clearance for shuttles 100 and 102, as well as first and second band collars 136 and 138. In this manner, multiple control functions for articulation and reticulation may be provided within handle 12 while keeping handle 12 compact and easily operable by a single hand of the user.

With reference to FIGS. 21 and 22, it can be appreciated that, reticulation assembly 36 (FIG. 19) may also be used to rotate end effector assembly 20 independently of articulation section 18 when articualtion section 18 is in a bent or articulated condition.

Thus, surgical instrument 10 incorporates rotational, articulation and roticulational functions in a compact handle 12 easily operable by a single hand of the user.

It will be understood that various modifications may be made to the embodiments disclosed herein. For example, different end effector assemblies, such as, for example, grasping, stapling, etc. may be provided on the disclosed surgical instrument. Further, as noted herein, the disclosed surgical instrument may incorporate cautery, optical or other capabilities. Additionally, it will be appreciated that the entire elongate tubular member may be rotated while the articulation section is in the articulated position. Therefore, the above description should not be construed as limiting, but merely as exemplifications of particular embodiments. Those skilled in the art will envision other modifications within the scope and spirit of the claims appended hereto.

The invention claimed is:
1. A surgical instrument comprising:
  a handle;
  an elongate tubular member extending distally from the handle and including an articulating section bendable relative to the remainder of the elongate tubular member; and
  an articulating mechanism for bending the articulating section, the articulating mechanism including:
    a flexible band having a proximal end and a distal end;
    a rotatable wheel mounted on the handle and spaced from the proximal end of the flexible band; and
    a shuttle interconnecting the rotatable wheel and the proximal end of the flexible band such that rotation of the wheel relative to the handle causes linear translation of the shuttle and translation of the band,
  wherein the wheel has a groove and the shuttle includes a pin movable within the groove in the wheel, the articulation section being configured such that translational movement of the band moves the articulation section from a first neutral position to a second bent position.

2. The surgical instrument as recited in claim 1, wherein the groove is in the form of a spiral.

3. The surgical instrument as recited in claim 2, wherein the spiral is in the form of an Archimedes spiral.

4. The surgical instrument as recited in claim 1, wherein the articulating mechanism includes a collar affixed to a proximal end of the band, the collar being engagable by the shuttle.

5. The surgical instrument as recited in claim 4, wherein the collar is engagable by a hook on the distal end of the shuttle.

6. The surgical instrument as recited in claim 4, wherein the collar is free to rotate relative to the shuttle.

7. The surgical instrument as recited in claim 1, wherein the articulation mechanism includes a first and a second band, the first and second bands engagable with respective first and second grooves formed in opposed sides of the wheel.

8. The surgical instrument as recited in claim 7, wherein the articulation mechanism includes first and second shuttles, proximal ends of the first and second shuttles engagable with the respective first and second grooves in the wheel.

9. The surgical instrument as recited in claim 8, wherein the first and second grooves are oriented in reverse directions on opposed sides of the wheel.

10. The surgical instrument as recited in claim 9, wherein the articulation mechanism includes first and second collars affixed to proximal ends of the first and second bands, the first and second collars engagable with the first and second shuttles such that rotation of the wheel reciprocates the first and second bands.

11. The surgical instrument as recited in claim 1, wherein the shuttle is configured to translate the proximal end of the band along an axis substantially parallel with an axis defined by the elongate tubular member.

12. The surgical instrument as recited in claim 1, wherein the wheel is at least partially disposed within the handle.

13. A surgical instrument comprising:
  a handle;
  an elongate tubular member defining a longitudinal axis and extending distally from the handle and including an articulating section bendable relative to the remainder of the elongate tubular member; and
  an articulating mechanism configured for bending the articulating section, the articulating mechanism including:

at least one flexible band having a proximal portion and a distal portion;

a shuttle coupled with the at least one flexible band; and a rotatable wheel mounted on the handle and being configured to engage the shuttle such that rotation of the wheel causes axial translation of the shuttle and at least one flexible band, the shuttle being restricted to linear movement within the handle, wherein the articulating section is configured for bending upon actuation of the shuttle and the at least one flexible band and the shuttle maintains the proximal portion of the at least one flexible band in a parallel arrangement with the longitudinal axis of the elongate tubular member.

14. The surgical instrument as recited in claim 13, wherein the wheel includes a groove configured to engage a portion of the shuttle.

15. The surgical instrument as recited in claim 14, wherein the shuttle includes a pin extending therefrom, the groove of the wheel configured to movably receive the pin.

16. The surgical instrument as recited in claim 15, wherein the wheel is configured to rotate relative to the pin such that an axial force is exerted on the pin when the pin is disposed in the groove.

* * * * *